(12) United States Patent
Moloney et al.

(10) Patent No.: US 9,578,882 B2
(45) Date of Patent: Feb. 28, 2017

(54) ANTIMICROBIAL COMPOUNDS

(71) Applicant: ISIS INNOVATION LIMITED, Oxford (GB)

(72) Inventors: Mark Moloney, Oxford (GB); Yong-chu Jeong, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 10 days.

(21) Appl. No.: 14/410,559

(22) PCT Filed: Jun. 25, 2013

(86) PCT No.: PCT/GB2013/051669
§ 371 (c)(1),
(2) Date: Dec. 22, 2014

(87) PCT Pub. No.: WO2014/001782
PCT Pub. Date: Jan. 3, 2014

(65) Prior Publication Data
US 2015/0313233 A1    Nov. 5, 2015

(30) Foreign Application Priority Data
Jun. 25, 2012   (GB) .................................. 1211202.5

(51) Int. Cl.
*A01N 43/90* (2006.01)
*C07D 498/04* (2006.01)
*C07D 513/04* (2006.01)

(52) U.S. Cl.
CPC ............. *A01N 43/90* (2013.01); *C07D 498/04* (2013.01); *C07D 513/04* (2013.01)

(58) Field of Classification Search
None
See application file for complete search history.

(56) References Cited

FOREIGN PATENT DOCUMENTS

CN      102050776     *  5/2011   ........... C07D 207/44

OTHER PUBLICATIONS

International Search Report and Written Opinion for PCT/GB2013/051669, Aug. 7, 2013, 12 pages.
Mark D. Andrews et al: "Highly Functionalised Pyroglutamates by Intramolecular Aldol Reactions: Towards the Pyroglutamate Skeleton of Oxazolomycin", Syn Lett, vol. 1996, No. 07, pp. 612-614, Jul. 1, 1997 (Jul. 1, 1996).
Andrew G. Brewster et al: "Stereoselective intramolecular aldol reactions of (4R)-3-(3-oxobutanoyl)-1,3-thiazolidine-4-carboxylates believed to be directed by 'self-induced' axial chirality", Chemical Communications, No. 3, 1998, pp. 299-300.
Brewster A G et al: "Memory of chirality effects in aldol cyclisations of 1-(3-oxobutyryl) derivatives of 1-4-oxaproline and I-praline isopropyl esters", Tetrahedron Letters, Elsevier, Amsterdam, NL, vol. 43, No. 21, pp. 3919-3922, May 20, 2002 (May 20, 2002).
Yong-Chul Jeong et al: "Control of chemoselectivity in Dieckmann ring closures leading to tetramic acids", Organic & Biomolecular Chemistry, vol. 9, No. 19, p. 6663, Jan. 1, 2011 (Jan. 1, 2011).
Chloe A. Holloway et al: "Novel Chiral Skeletons for Drug Discovery: Antibacterial Tetramic Acids", Chemical Biology & Drug Design, vol. 78, No. 2, pp. 229-235, Aug. 16, 2011 (Aug. 16, 2011).
Yong-Chul Jeong et al: "Natural product inspired antibacterial tetramic acid libraries with dual enzyme inhibition", Chemical Science, vol. 4, No. 3, p. 1008, Jan. 1, 2013 (Jan. 1, 2013).

* cited by examiner

*Primary Examiner* — Alicia L Otton
(74) *Attorney, Agent, or Firm* — Squire Patton Boggs (US) LLP

(57) ABSTRACT

The present invention relates to certain tetramic acid derivatives and, in particular, bicyclic tetramic acid derivatives that are suitable for use in the preparation and development of antimicrobial (e.g. antibacterial or antifungal) compositions. The present invention also relates to the use of such compounds as antimicrobial (e.g. antibacterial or antifungal agents) and, in particular, as topical antibacterial or antifungal agents.

22 Claims, No Drawings

ANTIMICROBIAL COMPOUNDS

The present invention relates to certain tetramic acid derivatives and, in particular, bicyclic tetramic acid derivatives that are suitable for use in the preparation and development of antimicrobial (e.g. antibacterial or antifungal) compositions. The present invention also relates to the use of such compounds as antimicrobial (e.g. antibacterial or antifungal agents) and, in particular, as topical antibacterial or antifungal agents.

As the use of antibiotics becomes increasingly widespread, antibiotic-resistant strains of bacteria have evolved. As a result, there is a growing need for new antibiotics to combat the continuous emergence of such resistant strains.

Natural products containing a tetramate nucleus are known and some of these compounds are known to exhibit antibacterial activity. For example, streptolydigin and tirandamycin are known to have antibacterial activity against Gram-positive and Gram-negative bacteria, while reutericyclin is bacteriostatic or bactericidal to Gram-positive bacteria.

Attempts have been made to use such natural product as starting points to identify synthetic compound libraries of antibacterial agents. Attempts have also been made to use the tetramate nucleus as a scaffold for designing compounds with antibacterial activity. Examples of such compounds are described in WO 2008/014311 and EP 1116715.

It is among the objects of embodiments of the present invention to provide alternative compounds that can be used for the preparation and/or development of antibacterial compositions, and, in particular, antibacterial compositions for topical use.

SUMMARY OF THE INVENTION

In one aspect of the present invention, there is provided a compound as defined herein.

In another aspect, the present invention provides an antimicrobial composition comprising a compound as defined herein. Preferably, the composition is a topical composition.

In another aspect, the present invention provides the use of a compound as defined herein as an antimicrobial agent, such as a preservative.

In another aspect of the present invention, there is provided a compound as defined herein for use as a medicament for treating a topical microbial infection, such as a bacterial or fungal infection.

The present invention further provides a method of synthesising a compound as defined herein.

The present invention also provides a method of inhibiting bacterial RNA polymerase and/or undecaprenyl pyrophosphate synthase, which method comprising contacting a cell with an effective amount of a compound as defined herein.

In another aspect, the present invention provides a compound obtainable by, or obtained by, or directly obtained by a method of synthesis as defined herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

In this specification, the term "hydrocarbyl" refers to any substituent that consists of carbon and hydrogen atoms. The hydrocarbyl group may be saturated or unsaturated, or aromatic or aliphatic. The hydrocarbyl group may also be cyclic, straight chain or branched. Cyclic hydrocarbyl groups include monocyclic and polycyclic groups. Polycyclic groups include fused ring and bridged ring systems.

In this specification the term "alkyl" includes cyclic and non-cyclic, such as straight and branched chain alkyl groups.

The term "alkenyl" refers to hydrocarbyl groups containing at least one C=C bond. Alkenyl groups include cyclic, straight chain and branched alkenyl groups.

The term "aryl" refers to substituents comprising a cyclic, e.g. monocyclic or polycyclic aromatic ring having at least 5 carbon atoms. The aryl group is preferably an aryl hydrocarbyl group. Examples of aryl groups include, but are not limited to, phenyl, biphenyl, naphthyl and the like. In one embodiment, the aryl group may include a linking group attached the cyclic or polycyclic aromatic ring. The linking group may be of the formula $-[CR_{14}R_{15}]_t-$, where t is an integer of from 0 to 12, and $R_{14}$ and $R_{15}$ are each independently selected from H or $C_1$ to $C_2$ alkyl. For example, the aryl group may be $-C_6H_5$ or $-CH_2C_6H_5$. Thus, if a particular substituent, such as a hydrocarbyl group, is substituted with an aryl group, the substitution may take place via the linking group.

The term "halo" refers to fluoro, chloro, bromo and iodo.

The term "haloalkyl" is used herein to refer to an alkyl group in which one or more hydrogen atoms have been replaced by halogen atoms. The term "trihaloalkyl" refers to alkyl groups in which three hydrogen atoms have been replaced by halogen atoms, such as fluoroatoms. An example of a trihaloalkyl is trifluoroalkyl, $-CF_3$.

The term "heterocyclyl", "heterocyclic" or "heterocycle" covers aromatic, non-aromatic, saturated or unsaturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from at least one of nitrogen, oxygen or sulphur in the ring. Bicyclic heterocycles contain from about 7 to about 17 ring atoms, suitably from 7 to 12 ring atoms. Bicyclic heterocyclic(s) rings may be fused, spiro, or bridged ring systems. Where the heterocycle comprises two or more ring structures, a heteroatom may be present in one or more of the rings. In one embodiment, the heterocycle group may include a linking group attached thereto. The linking group may be of the formula $-[CR_{14}R_{15}]_t-$, where t is an integer of from 0 to 12, and $R_{14}$ and $R_{15}$ are each independently selected from H or $C_1$ to $C_2$ alkyl. Thus, if a particular substituent, such as a hydrocarbyl or heterocyclic group, is substituted with another heterocyclic group, the substitution may occur via the linking group.

As the skilled person would appreciate, any heterocycle may be linked to another group via any suitable atom, such as via a carbon or nitrogen atom.

By "bridged ring systems" is meant ring systems in which two rings share more than two atoms, see for example *Advanced Organic Chemistry*, by Jerry March, 4th Edition, Wiley Interscience, pages 131-133, 1992.

As discussed above, the heterocyclic group may be an aromatic heterocyclic group (hereinafter a "heteroaryl" group). Examples of such heteroaryls include aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings.

The term "optionally substituted" refers to either groups, structures, or molecules that are substituted and those that are not substituted.

Where optional substituents are chosen from "one or more" groups, it is to be understood that this definition includes at least one of the substituents being chosen from one of the specified groups or two or more of the substituents being chosen from two or more of the specified groups. It is not necessary for all substituents to be chosen from one of the specified groups, although this may be preferred.

The phrase "compound of the invention" means those compounds which are disclosed herein, both generically and specifically. For the avoidance of doubt, the term "compound" covers the compound per se, as well as salts (including pharmaceutically acceptable salts) and solvates thereof.

It is to be appreciated that references to "treating" or "treatment" include prophylaxis as well as the alleviation of established symptoms of a condition, such as a bacterial or fungal infection. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Tetramic Acid Derivatives

The present invention provides a compound of the formula I or II below:

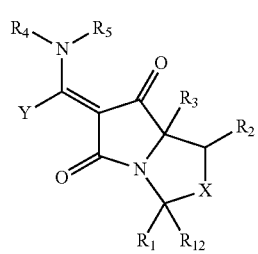

Formula I

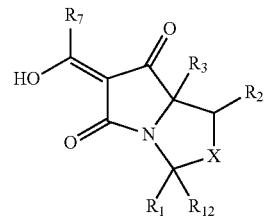

Formula II wherein:
X is O, S or $SO_2$,
Y is OH or $C_1$ to $C_{10}$ alkyl,
$R_1$, $R_2$ and $R_4$ are each independently selected from H and $C_1$ to $C_6$ alkyl,
$R_3$ is selected from a functional group selected from H, $C_1$ to $C_6$ alkyl, and a carbonyl-containing group,
$R_{12}$ is H, alkenyl, aryl, trihaloalkyl and $C_1$ to $C_6$ alkyl,
$R_5$ and $R_7$ are each a group of the formula $L_1$-$L_2$-$R_6$ or $L_2$-$L_1$-$R_6$,
where $L_1$ is a linker of the formula $-[CR_8R_9]_{12}-$, where n is an integer of from 0 to 12, and $R_8$ and $R_9$ are each independently selected from H or $C_1$ to $C_2$ alkyl, and
where $L_2$ is absent or a linker that is selected from O, S, SO, $SO_2$, N(R'), C(O), C(O)O, OC(O), $[O(CR'_2)_r]_s$, $[(CR'_2)_rO]_s$, CH(OR'), C(O)N(R'), N(R')C(O), N(R')C(O)N(R'), $SO_2N(R')$ or $N(R')SO_2$ where R' and R" are each independently selected from hydrogen and a $C_1$ to $C_2$ alkyl, and where r is 1 or 2 and s is 1 to 4, and
where $R_6$ is selected from $OR^{13}$, heterocyclic and $C_1$ to $C_{25}$ hydrocarbyl group, wherein $R^{13}$ is a $C_1$ to $C_6$ alkyl, and said heterocyclic and hydrocarbyl group is optionally substituted with at least one functional group selected from alkenyl, alkyl, aryl, halo, trihaloalkyl, alcohol, keto, $S(O)R^{13}$, sulfonyl, thio-alcohol, ester, thioester, ether, thioether, amide, thioamide, urea, thiourea, =O, =S, amine and heterocyclic group.

Preferably, the compound has the formula:

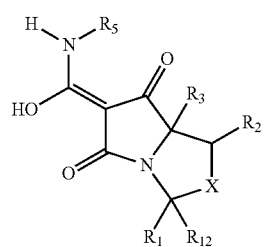

Formula Ia or

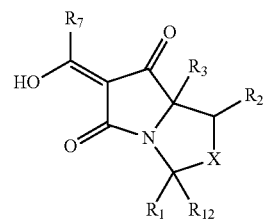

Formula II

More preferably, the compound has the Formula Ia above.
In a preferred embodiment, Y is OH. Accordingly, it is preferred that Y is not a $C_1$ to $C_{10}$ alkyl.

The compounds of the present invention are useful in the development and/or manufacture of anti-microbial compositions, such as anti-bacterial or anti-fungal compositions. Without wishing to be bound by any theory, the antimicrobial activity is believed to be at least partially attributable to the [3.3.0] bicyclic structure and the substituent at the 7 position of the bicyclic ring structure. The antimicrobial activity may also depend on the nature of the substituents at at least one of the X, $R_2$, $R_3$, $R_1$ and $R_{12}$ positions. By varying at least one of these substituents, the antimicrobial activity of the compound may be optimised. Accordingly, the present invention provides the means for developing and optimising lead compounds for the synthesis of antimicrobial (e.g. antibacterial or antifungal) actives. In another embodiment, the present invention provides compounds for use as antimicrobial actives, and, in particular, antibacterial actives for topical use.

Preferably, X is O or S.

Preferably, Y is OH.

In one embodiment, $R_4$ is H. In another embodiment, $R_1$ is H or a $C_1$ to $C_4$ alkyl, such as methyl, ethyl, propyl (i-propyl or n-propyl) or butyl (n-butyl, t-butyl, s-butyl and i-butyl, preferably t-butyl). In another embodiment, both $R_1$ and $R_4$ are H. $R_2$ may be H or a $C_1$ to $C_6$ alkyl, preferably a $C_1$ to $C_3$ alkyl. Where $R_2$ is a $C_1$ to $C_6$ alkyl, methyl, ethyl and propyl (i-propyl or n-propyl) are preferred.

$R_3$ may be H, $C_1$ to $C_6$ alkyl or a carbonyl-containing group. Where $R_3$ is an alkyl group, the alkyl is preferably a $C_1$ to $C_3$ alkyl, more preferably methyl or ethyl. Where $R_3$ is a carbonyl-containing group, the carbonyl-containing group may include an ester or ketone group. Suitable esters include —COOR$_z$, where R$_z$ is an alkyl, preferably a $C_1$ to $C_6$ alkyl, more preferably methyl or ethyl. In one embodiment, R$_z$ is a $C_1$ to $C_6$ alkyl that is substituted with an ether group, such as an OCH$_3$ or OC$_2$H$_5$ group. For example, R$_z$ may be —CH$_2$CH$_2$OCH$_3$.

Where $R_3$ is a ketone group, it may have the formula —C(O)R$_y$, where R$_y$ is a $C_1$ to $C_6$ alkyl group. In one embodiment, $R_3$ is selected from —C(O)C$_2$H$_5$ and —C(O)C$_4$H$_9$.

In one embodiment, $R_2$ is CH$_3$ and $R_3$ is H, or $R_3$ is CH$_3$ and $R_2$ is H. Alternatively, $R_2$ is H or methyl and $R_3$ is —COOR$_z$, where R$_z$ is an alkyl, such as a methyl or ethyl group.

As mentioned above, $R_{12}$ is selected from H, alkenyl, aryl, trihaloalkyl and $C_1$ to $C_6$ alkyl. In particular, the alkenyl and aryl groups may be substituted, for example, with one or more halo groups (such as F, Cl, Br and/or I), nitro groups, TBDMSO or ether groups (OCH$_3$, OC$_2$H$_5$ or OPh). Preferably, at least one of $R_1$ and $R_{12}$ is H. Where $R_{12}$ is an alkenyl group, the alkenyl group may include 1 to 8 carbon atoms, preferably 1 to 6 carbon atoms. The alkenyl group may include one or more double bonds. An example of a suitable alkenyl group is —C(CH$_3$)$_2$CH$_2$CH=CH$_2$.

Where $R_{12}$ is a trihaloalkyl, the trihaloalkyl may include 1 to 3 carbon atoms, preferably 1 carbon atom. The halo group may be F, Cl, Br or I but F is preferred. An example of a suitable trihaloalkyl group is trifluoromethyl. Where $R_{12}$ is a $C_1$ to $C_6$ alkyl group, the alkyl group is preferably a $C_1$ to $C_4$ alkyl group, such as methyl, ethyl, propyl (i-propyl or n-propyl) or butyl (n-butyl, t-butyl, s-butyl and i-butyl, preferably t-butyl). Where $R_{12}$ is an aryl group, the aryl group may be phenyl. The aryl group may be substituted, for example, with one or more halo groups, such as F, Cl or Br. Other substituents include nitro substituents and TBDMSO. Examples of suitable $R_{12}$ include:

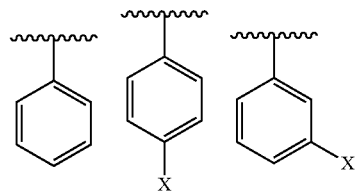

where X is selected from F, Cl, Br, NO$_2$ and CH$_2$TBDMSO, and

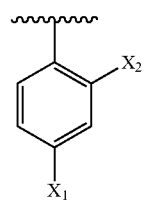

where $X_1$ and $X_2$ are independently selected from F, Br and Cl. In one embodiment, $X_1$ is F and $X_2$ is Cl.

In one embodiment, $R_1$ is t-butyl and $R_{12}$ is H. In another embodiment, $R_1$ is trifluoromethyl and $R_{12}$ is H or methyl. In another embodiment, $R_{12}$ is CH$_2$=CHCH$_2$C(CH$_3$)$_2$ and $R_1$ is H. In yet another embodiment, $R_{12}$ may be C$_6$H$_3$F$_2$ and $R_1$ may be H.

$R_5$ and $R_7$ are each a group of the formula L$_1$-L$_2$-R$_6$ or L$_2$-L$_1$-R$_6$, L$_1$-L$_2$-R$_6$ being preferred. As noted above, L$_1$ is a linker of the formula —[CR$_8$R$_9$]$_n$—, where n is an integer of from 0 to 12, and R$_8$ and R$_9$ are each independently selected from H or $C_1$ to $C_2$ alkyl. Preferably, n is from 0 to 11, more preferably 0 to 6, even more preferably 0 to 4, for example, 0 or 1. Preferably, R$_8$ and R$_9$ are each independently selected from H or methyl. Where more than one —[CR$_8$R$_6$]— link is present (i.e. n is greater than 1), R$_8$ may be the same or different in each instance of —[CR$_8$R$_9$]—. Similarly, R$_9$ may be the same or different in each instance of —[CR$_8$R$_9$]—.

As noted above, L$_2$ may be absent or a linker that is selected from O, S, SO, SO$_2$, N(R'), C(O), C(O)O, OC(O), [O(CR'$_2$)$_r$]$_s$, [(CR'$_2$)$_r$O]$_s$CH(OR'), C(O)N(R'), N(R')C(O), N(R')C(O)N(R'), SO$_2$N(R') or N(R')SO$_2$ where R' and R" are each independently selected from hydrogen and a $C_1$ to $C_2$ alkyl, and where r is 1 or 2 and s is 1 to 4. In one embodiment, L$_2$ is absent. In another embodiment, L$_2$ is selected from O, C(O)O, OC(O), C(O)N(R') and N(R')C(O).

As mentioned above, R$_6$ is selected from OR$^{13}$, heterocyclic and $C_1$ to $C_{25}$ hydrocarbyl group. Where R$_6$ is OR$^{13}$, R$^{13}$ is a $C_1$ to $C_6$ alkyl, preferably a $C_1$ to $C_4$ alkyl group, such as methyl, ethyl, propyl (i-propyl or n-propyl) or butyl (n-butyl, t-butyl, s-butyl and i-butyl, preferably t-butyl).

R$_6$ may be a heterocyclic group. Suitable heterocyclic groups include aromatic and non-aromatic, saturated and unsaturated, and monocyclic and polycyclic heterocycles. Such groups may contain one or more heteroatoms, such as O, N and S. Where two or more heteroatoms are present, these may be the same or different. Where polycyclic heterocycles are used, the heteroatom may be present in one or more (e.g. all) of the cyclic groups. The heterocyclic group preferably has 5 to 12 ring members, for example, 5, 6, 7, 8 or 9 ring members. Suitable heterocyclic groups include saturated heterocyclic groups comprising 1 or 2 heteroatoms selected from O, N and S, preferably O and N.

Examples of such saturated heterocycles include tetrahydrofuranyl, oxanyl, pyrrolidinyl, piperidinyl, azepanyl, morpholinyl, dioxanyl and piperazinyl. Suitable heterocyclic groups also include saturated heterocyclic groups comprising 1 or 2 heteroatoms selected from O, N and S. Examples of such unsaturated heterocycles include furanyl, pyrrol, imidazolyl, pyrazolyl, thiazolyl, isothiazolyl, diazinyl. The heterocycles may be fused to another ring, such as a cyclohexyl ring or benzene ring. Examples of such fused heterocycles include indole, isoindole and benzothiazole. The heterocyclic group may or may be coupled to the nitrogen of the enamine group, $L_1$ or $L_2$ via the heteroatom. Alternatively, the attachment may be via a C atom.

$R_6$ may be a $C_1$ to $C_{25}$ hydrocarbyl group. This may be saturated or unsaturated, or aromatic or aliphatic. The hydrocarbyl group may be cyclic, straight chain or branched. In one embodiment, $R_6$ is an alkyl group. Suitable alkyl groups include straight chain alkyl groups, such as those of the formula $C_iH_{2i+1}$, where i is 1 to 22, preferably 6 to 19. Cyclic alkyl groups, including monocyclic, polycyclic and bridged cycloalkyls, may also be used. Suitable monocyclic cycloalkyl groups may comprise $C_3$ to $C_6$ cycloalkyl groups, such as cyclopropane, cyclobutane, cyclopentyl and cyclohexyl. Such groups may also include hydrocarbyl linking groups, such as those of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Suitable bridged cycloalkyls include adamantyl (e.g. 1-adamantyl), myrtanyl, norborane and 6,6-dimethylbicyclo[3.1.1]heptan-2-yl)methyl. Adamantyl is particularly preferred. This substituent may be substituted preferably with alkyl groups, such as methyl or ethyl groups. Where an adamantyl is used, it may be substituted with an alkyl group, such as a methyl group, at the 1 and/or 2 position. The hydrocarbyl substituents may also include hydrocarbyl linking groups, such as those of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

In another embodiment, the hydrocarbyl group may be or include an aryl group. Suitable aryl groups may have 6 to 12 carbon atoms. A preferred example is phenyl. The phenyl group may optionally be substituted, for example, with alkyl groups and/or halo groups, such as F, Cl and Br. These aryl groups may also include hydrocarbyl linking groups, such as those of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

In another embodiment, the hydrocarbyl may be or include an alkenyl group. Such groups may be derived from the alkyl groups defined in, for example, paragraphs above by replacing at least one C—C bond with a C=C bond. A specific example is 1-cyclohexene. Such alkenyl groups may also include hydrocarbyl linking groups, such as those of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

As mentioned above, the heterocyclic group or hydrocarbyl group may be substituted with at least one functional group selected from alkenyl, alkyl, aryl, halo, trihaloalkyl, alcohol, keto, thioketo, sulfonyl, thio-alcohol, ester, thioester, ether, thioether, amide, thioamide, urea, thiourea, =O, =S, sulfonyl and heterocyclic groups. These substituents, particularly, the aryl and heterocyclic groups may themselves be substituted further, for example, with alkenyl, alkyl, aryl, halo, trihaloalkyl, alcohol, keto, thioketo, sulfonyl, thio-alcohol, ester, thioester, ether, thioether, amide, thioamide, urea, thiourea, =O, =S, sulfonyl and heterocyclic groups, such as those described herein. Where the heterocyclic group or hydrocarbyl group is substituted, at least one substituent must be selected from alkenyl, alkyl, aryl, halo, trihaloalkyl, alcohol, keto, $S(O)R^{13}$, sulfonyl, thio-alcohol, ester, thioester, ether, thioether, amide, thioamide, urea, thiourea, =O, =S, amine and heterocyclic groups. Where two or more substituents are present on the heterocyclic group or hydrocarbyl group, the second and one or more or all of the subsequent substituents may also be selected from alkenyl, alkyl, aryl, halo, trihaloalkyl, alcohol, keto, $S(O)R^{13}$, sulfonyl, thio-alcohol, ester, thioester, ether, thioether, amide, thioamide, urea, thiourea, =O, =S, amine and heterocyclic groups.

The heterocyclic group or hydrocarbyl group may be substituted with any alkenyl group. Suitable alkenyl groups are those having at least one C=C bond. The C=C may be coupled directly to the heterocyclic group or hydrocarbyl group or via a linking group of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3. The alkenyl group may have 2 to 20 carbon atoms, for example, 2 to 6 carbon atoms. The alkenyl group may be cyclic, straight chain or branched.

Where the substituent is an alkyl group, cyclic, straight chain and branched alkyl groups may be used. Suitable alkyl substituents may have 1 to 20 carbon atoms, for example, 1 to 6 carbon atoms. Preferred alkyl groups include methyl, ethyl, propyl (i-propyl or n-propyl) or butyl (n-butyl, t-butyl, s-butyl and i-butyl).

Where the substituent is an aryl group, the aryl group may be or include a hydrocarbyl aryl. Examples of aryl groups include, but are not limited to, phenyl, biphenyl, naphthyl and the like. Phenyl is preferred. In one embodiment, the aryl group may include a linking group attached the cyclic or polycyclic aromatic ring. The linking group may be of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3. For example, the aryl group may be —$C_6H_5$ or —$CH_2C_6H_5$. The aryl group may itself be substituted, for example, with alkyl, aryl, halo, trihaloalkyl, alcohol, keto, thioketo, sulfonyl, thio-alcohol, ester, thioester, ether, thioether, amide, thioamide, urea, thiourea, =O, =S, sulfonyl and heterocyclic groups as described herein. Examples of suitable substituents include alkyl groups, such as $CH_3$, $C_2H_5$ and t-butyl groups. Other examples include $OCH_3$, $OC_2H_5$ and OPh, phenyl, —OH, $(CH_2)_gOH$, where g is 1 to 3, $OCH_3$, $OC_2H_5$, OPh, $SCH_3$, $SC_2H_5$, SPh, $NH_2N(CH_3)_2$, F, Cl, Br, $CF_3$, $C(O)CH_3$ and $S(O)CH_3$.

Where the substituent is halo, it may be a F, Cl, Br or I group. One or more halo substituents may be present. Where more than one halo substituent is present, the halo groups may be the same or different.

Where the substituent is a trihaloalkyl, the trihaloalkyl may be a trihalo($C_1$-$C_6$)alkyl. The halo substituent may be F, Cl, Br or I. The three halo substituents may be the same or different. Preferably, the trihaloalkyl is trihalomethyl, more preferably trifluoromethyl.

Where the substituent is an alcohol or a thioalcohol, the OH or SH substituent may be coupled directly to the heterocyclic or hydrocarbyl group. Alternatively, the OH substituent may be coupled to the heterocyclic or hydrocarbyl group via, for example, —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is an ester, the substituent may have the formula $C(O)OR_{16}$ or $OC(O)R_{16}$, where $R_{16}$ is a $C_1$ to $C_6$ alkyl (preferably methyl or ethyl), benzyl or phenyl group. Where the substituent is a thioester, the substituent may have the formula $C(O)SR_{16}$ or $SC(O)R_{16}$. The $C(O)OR_{16}$, $OC(O)R_{16}$ or $C(O)SR_{16}$ or $SC(O)R_{16}$ thioester may be coupled directly to the heterocyclic group or hydrocarbyl group or via a linking group, for example, of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is an ether, the ether substituent may have or may include a group having the formula $OR_{17}$, where $R_{17}$ is $C_1$ to $C_6$ alkyl, phenyl or benzyl. Preferably, $R_{17}$ is a methyl, ethyl, propyl (i-propyl or n-propyl) or butyl (n-butyl, t-butyl, s-butyl and i-butyl). Preferred ether substituents include $OCH_3$, $OC_4H_9$, $OCH(CH_3)_2$ and OPh. The $OR_{17}$ group may be coupled directly to the heterocyclic group or hydrocarbyl group or via a linking group, for example, of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is a thioether, the thioether substituent may or may include a group having the formula $SR_{17}$, where $R_{17}$ is $C_1$ to $C_6$ alkyl, phenyl or benzyl. A preferred thioether substituent is SMe. The $SR_{17}$ group may be coupled directly to the heterocyclic group or hydrocarbyl group or via a linking group e.g. of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is amide, the amide may have or may include a group of the formula $N(R_{18})C(O)R_{19}$ or $C(O)NR_{18}R_{19}$. $R_{18}$ may be selected from H and $C_1$ to $C_{10}$ alkyl, while $R_{19}$ may be a $C_1$ to $C_{15}$ alkyl, trihaloalkyl (e.g. a trihalo($C_1$-$C_{15}$)alkyl) or $OR_{20}$, where $R_{20}$ is a $C_1$ to $C_6$ alkyl. In one embodiment, $R_{18}$ is H or $C_1$ to $C_6$ alkyl. Examples of suitable amide groups include $HNC(O)C_9H_{19}$, $HNC(O)OC(CH_3)_3$, $HNC(O)C_6F_{13}$, $C(O)N(C_6H_{13})(C_6H_{13})$, $HNC(O)Ph$, $N(CH_3)C(O)C_{11}H_{23}$, and HNC(O)1-adamantyl. The $N(R_{18})C(O)R_{19}$ or $C(O)NR_{18}R_{19}$ group may be coupled directly to the heterocyclic group or hydrocarbyl group or via a linking group e.g. of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is thioamide, the thioamide may have or may include a group having the formula $N(R_{18})C(S)R_{19}$ or $C(S)NR_{18}R_{19}$. The $N(R_{18})C(S)R_{19}$ or $C(S)NR_{18}R_{19}$ group may be coupled directly to the heterocyclic group or hydrocarbyl group or via a linking group e.g. of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is urea, it may have the formula $R_{30}C(O)R_{31}R_{32}$, where $R_{30}$, $R_{31}$ and $R_{32}$ are independently selected from H and $C_1$ to $C_6$ alkyl, for example, methyl or ethyl.

Where the substituent is thiourea, it may have the formula $R_{30}C(S)R_{31}R_{32}$, where $R_{30}$, $R_{31}$ and $R_{32}$ are independently selected from H and $C_1$ to $C_6$ alkyl, for example, methyl or ethyl.

Where the substituent is a keto (or alkanoyl) group, it may have or may include a group of the formula $C(O)R_{20}$, where $R_{20}$ is a $C_1$ to $C_6$ alkyl, such as a methyl, ethyl, propyl (i-propyl or n-propyl) or butyl (n-butyl, t-butyl, s-butyl and i-butyl). An example of a suitable keto group is a $C(O)CH_3$ group. In one embodiment, the keto group comprises an oxo substituted cycloalkyl group. The cycloalkyl group may have 4 to 8 carbon atoms, for example, 5 or 6 carbon atoms. The $C(O)R_{20}$ group may be coupled directly to the hydrocarbyl group or heterocyclic group or may be coupled via a linker, for example, of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is of the formula $S(O)R_{13}$, $R_{13}$ may be $C_1$ to $C_6$ alkyl, preferably methyl. The $S(O)R_{13}$ may be coupled directly to the hydrocarbyl group or heterocyclic group or may be coupled via a linker, for example, of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is a sulfonyl, it may include a substituent having the formula $SO_2R_{21}$, where $R_{21}$ is a $C_1$ to $C_6$ alkyl or a trihalo($C_1$ to $C_6$) alkyl, such as trifluoroalkyl. These groups may be coupled directly to the hydrocarbyl or heterocyclic group or via a linker, such as one of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is an =O (oxo) or =S group, these are typically coupled to a ring atom of, for example, a heterocyclic, aryl or cyclic hydrocarbyl (e.g. alkyl or alkenyl) group. In one embodiment, an =O substituent is provided on a cyclopentyl ring.

Where the substituent is an amine, the amine may be or comprise a group of the formula $NR_{22}R_{23}$, where $R_{22}$ and $R_{23}$ are independently selected from H and $C_1$ to $C_6$ alkyl. In one embodiment, both $R_{22}$ and $R_{23}$ are H. In another embodiment, $R_{22}$ and $R_{23}$ are independently selected from H, methyl and ethyl. Examples of preferred amine substituents are $NH_2$, $N(CH_3)_2$ and $N(C_2H_5)_2$. The amines may optionally be provided in salt form, for example, as a salt of HCl. The $NR_{22}R_{23}$ group may be coupled directly to the heterocyclic or hydrocarbyl group or may be coupled via a linking group, such as one of the formula —[$CR_{14}R_{15}$]$_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

Where the substituent is a heterocyclic group, it may be or may include aromatic and non-aromatic, saturated and unsaturated, and monocyclic and polycyclic heterocycles. Such groups may contain one or more heteroatoms, such as O, N and S. Where two or more heteroatoms are present, these may be the same or different. Where polycyclic heterocycles are used, the heteroatom may be present in one or more (e.g. all) of the cyclic groups. The heterocyclic group preferably has 5 to 12 ring members, for example, 5, 6, 7, 8 or 9 ring members. Suitable heterocyclic groups include saturated heterocyclic groups comprising 1 or 2 heteroatoms selected from O, N and S, preferably O and N. Examples of such saturated heterocycles include tetrahydrofuranyl, oxanyl, pyrrolidinyl, piperidinyl, azepanyl, morpholinyl, dioxanyl and piperazinyl. Suitable heterocyclic groups also include saturated heterocyclic groups comprising 1 or 2 heteroatoms selected from O, N and S. Examples of such unsaturated heterocycles include furanyl, pyrrol, imidazolyl, pyrazolyl, thiazolyl, isothiazolyl, diazinyl. The heterocycles may be fused to another ring, such as a cyclohexyl ring or benzene ring. Examples of such fused heterocycles include indole, isoindole and benzothiazole. The heterocyclic group may be coupled directly to the hydrocarbyl or heterocyclic group coupled to the enamine nitrogen. Alternatively, the heterocyclic group may be coupled indirectly via a linking group, such as one of the formula —$[CR_{14}R_{15}]_t$—, where t is an integer of from 0 to 12, and $R_{14}$ and $R_{15}$ are each independently selected from H or $C_1$ to $C_2$ alkyl. Preferably, t is an integer from 0 to 6, for example, 1 to 3.

The heterocyclic group may itself be substituted. Suitable substituents are alkyl, aryl, alcohol, ether, thioether, amine, halo, trihaloalkyl, trihaloalkylether, keto, $S(O)R_{25}$, where $R_{25}$ is a $C_1$ to $C_6$ alkyl. These substituents are as defined herein. However, specific examples of such substituents include methyl, ethyl, phenyl, —OH, $(CH_2)_g$OH, where g is 1 to 3, $OCH_3$, $OC_2H_5$, OPh, $SCH_3$, $SC_2H_5$, SPh, $NH_2N(CH_3)_2$, F, Cl, Br, $CF_3$, $C(O)CH_3$ and $S(O)CH_3$.

In a preferred embodiment, $R_6$ is a phenyl group that is optionally substituted with at least one functional group selected from alkyl, aryl, halo, trihaloalkyl, alcohol, thioalcohol, ester, thioester, ether, thioether, amide, thioamide, urea, thiourea and heterocyclic group.

The phenyl group may be substituted with a group selected from cyclohexyl, to $C_3$ alkyl, halo, halo($C_1$ to $C_3$) alkyl, OH, SH, heterocyclic and $OR_{10}$ or $SR_{10}$, where $R_{10}$ is a $C_1$ to $C_4$ alkyl or phenyl group. Preferably, however, the phenyl group is substituted with a heterocyclic group selected from a piperidine and morpholine group, or where the phenyl group is fused to an aromatic heterocyclic ring, preferably a pyrrole ring.

In another preferred embodiment, the compound has the formula:

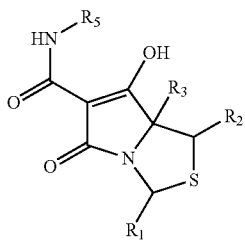

wherein $R_5$ is selected from 1-adamantyl and $CH_2$—$C_6H_5$, or

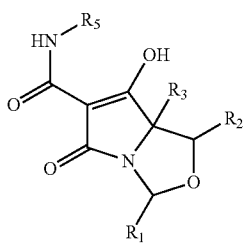

wherein $R_5$ is $CH_2$—$C_6H_5$.

In another preferred embodiment, the compound has the formula

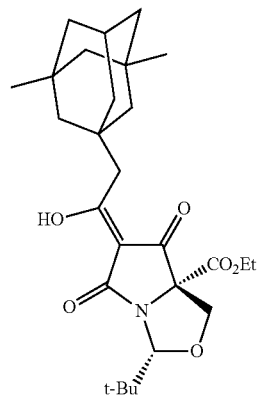 [SMILES: CCOC(=O)[C@]12CO[C@H](C(C)(C)C)N1C(=O)/C(=C(\O)CC13CC4CC(C)(CC(C)(C4)C1)C3)C2=O]

In one embodiment, the following requirements are met:
X=O or S; $R_1$=t-Bu or $CF_3$; $R_{12}$=H or Me; $R_2$=H, Me; $R_3$=H, Me, $CO_2$Me, $CO_2$Et, $CO_2(CH_2)_2$OMe, COEt, COBu; $R_6$ comprises adamantyl and substituted (e.g. with one or more methyl groups) adamantyl, cyclohexylmethyl, 6,6-dimethylbicyclo[3.1.1]heptan-2-yl)methyl, C6 to C13 alkyl, substituted aryl (e.g. 2-methyl-4-chlorophenyl, 2,4-dichlorophenyl, and 4-(trifluoromethyl)phenyl), In an embodiment of the present invention, the compound has the Formula Ia and the following requirements are met:
X=O or S; $R_1$=t-Bu or $CF_3$; $R_{12}$=H or Me; $R_2$=H or Me; $R_3$=H, Me; $R_6$ comprises at least one of adamantyl and substituted (e.g. with one or more methyl groups) adamantyl, cyclohexylmethyl, 6,6-dimethylbicyclo[3.1.1]heptan-2-yl)methyl, C6 to C12 alkyl, substituted aryl (e.g. 2-methyl-4-chlorophenyl, 2,4-dichlorophenyl, and 4-(trifluoromethyl)phenyl) and/or $(CH_2)_2$OPh.

In another embodiment, the compound has the Formula II and the following requirements are met:
X–O or S; $R_1$=t-Bu; $R_{12}$=H; $R_2$=H or Me; $R_3$=H, Me, $CO_2$Me, $CO_2$Et, $CO_2(CH_2)_2$OMe, COEt, COBu; $R_6$ comprises at least one of adamantyl and substituted adamantyl (e.g. substituted with a $C_1$ to $C_6$ alkyl group, such as methyl), and C6 to C13 alkyl.

In yet another embodiment, the compound has the Formula I where Y is a $C_1$ to $C_{10}$ alkyl and the following requirements are met:
X=O; $R_1$=t-Bu; $R_{11}$=H; $R_2$=H; $R_3$=Me, $CO_2$Me; $R_4$=H; $R_5$=$(CH_2)_2$OPh; Y=Me, or
X=O; $R_1$=t-Bu; $R_{11}$=H; $R_2$=H; $R_3$=Me, $CO_2$Me; $R_4$=H; $R_5$=C4 alkyl or a $C_4$ alkyl substituted with an ether group; Y=C9 alkyl.

Suitable or preferred features of any compounds of the present invention may also be suitable features of any other aspect.

A suitable pharmaceutically acceptable salt of a compound of the invention is, for example, a magnesium salt of the compound.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof.

It is also to be understood that certain compounds of the invention may exist in solvated as well as unsolvated forms such as, for example, hydrated forms. It is to be understood that the invention encompasses all such solvated forms.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below).

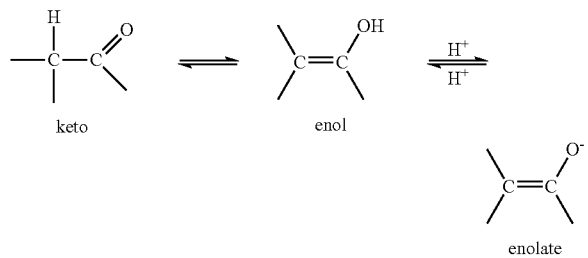

It shall also be appreciated that compounds of the present invention may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

The compounds of the present invention are useful as antimicrobial (e.g. antibacterial or antifungal agents). Accordingly, a further aspect of the present invention provides an antimicrobial composition, preferably a topical antibacterial or antifungal composition, comprising a compound as defined herein. As discussed above, the reference to "compound" covers all isomers of that compound as well as salts and solvates thereof.

The compounds of the present invention may be used as an antimicrobial compound in paper, fabric, building materials, packaging materials, coating and paint compositions, disinfectants, detergents, household products, cosmetics and suncreams.

The compounds of the present invention may be capable of inhibiting bacterial RNA polymerase and/or undecaprenyl pyrophosphate synthase. Accordingly, a further aspect of the invention provides a method of inhibiting bacterial RNA polymerase and/or undecaprenyl pyrophosphate synthase, which comprises contacting a cell with an effective amount of a compound as defined herein (or a pharmaceutically acceptable salt thereof). This contacting step may be performed ex-vivo or on the surface of a human or animal's skin.

The compounds of the present invention may be effective against Gram positive and/or Gram negative bacteria. For example, the compounds may be effective against Gram positive bacteria selected from at least one of Methicillin-resistant S. Aureus; Penicillin and erythromycin-resistant S. pneumonia; Vancomycin resistant E. Faecium; and Vancomycin susceptible E. Faecalis. Alternatively or additionally the compounds may be effective against Gram negative bacteria, such as H. influenzae. Some embodiments of the present invention are active against Gram positive bacteria but only weakly active against Gram negative bacteria. Preferred embodiments of the present invention are especially active against bacteria, such as MRSA (Methicillin resistant Staphylococcus aureus), MDR (multi-drug resistant bacteria), PRSP (Penicillin resistant Streptococcus pneumoniae) and VRE (Vancomycin resistant enterococcus).

In a preferred embodiment, the compounds of the present invention exhibit a minimum inhibitory concentration (MIC) of 16 µg/ml or less, preferably 12 µg/ml or less, more preferably 10 µg/ml or less, even more preferably 8 µg/ml or less, yet more preferably 6 µg/ml or less. In one embodiment, the MIC is 4 µg/ml or less, preferably less than 4 µg/ml or less, for example, 2 µg/ml or less. The compounds may exhibit the above MIC's against at least one bacteria selected from Gram positive and Gram negative bacteria. Examples of bacteria are discussed herein.

Procedures for determining MIC are well known in the art. For example, for bacteria, MICs may be determined based the Clinical and Laboratory Standards Institute (CLSI) methodology (Methods for dilution antimicrobial susceptibility tests for bacteria that grow aerobically; Approved Standard—seventh edition. 2006, M7-A7, CLSI, Wayne Pa.) by a 2-fold broth dilution technique in Mueller Hinton (pH7.4 Biorad). Overnight cultures may be diluted to obtain the final inoculum of 105 cfu/well. Incubation was 37° C. overnight in ambient air. The MIC may be defined as the lowest concentration which inhibited all visual growth and expressed in µg/ml. For each bacterial species, all of the molecules were tested in the same experiment in order to give a head-to-head comparison.

For fungi, MICs may be determined for the antifungus by microdilution methods using RPMI 1640 medium buffered with morpholinopropanesulfonic acid (MOPS) and supplemented with L-glutamine as described by CLSI procedures (M27-A method) (Reference method for broth dilution antifungal susceptibility testing of yeasts; Approved standard—third edition. 2006, M27-A2, CLSI, Wayne Pa.). After incubation for 24-48 hours at 35° C., the lowest concentration of drug which produced 80% reduction in visible growth compared with control may be considered as the MIC.
Preferred examples of the compounds of the present invention are as follows:
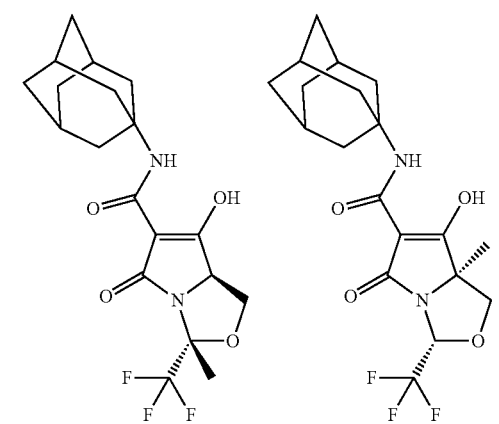
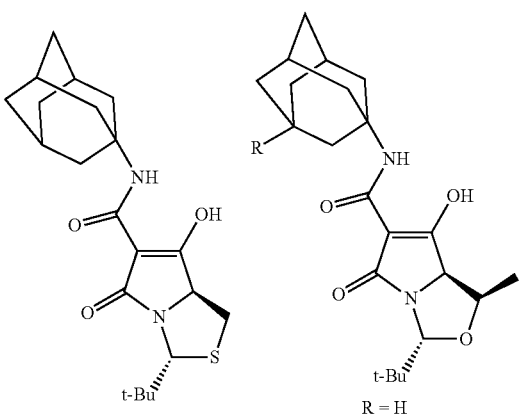
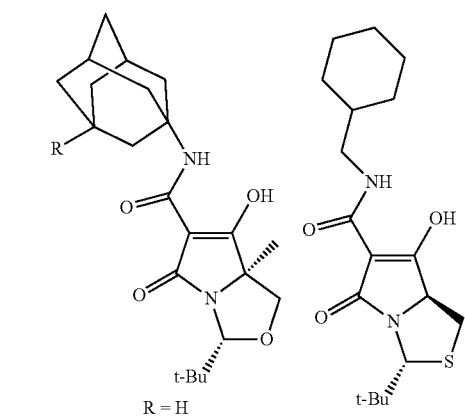
-continued
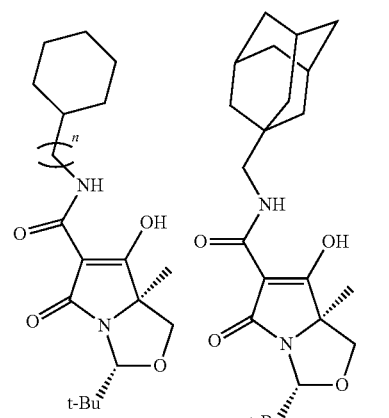
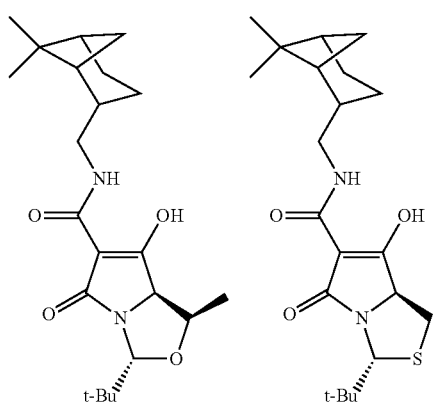
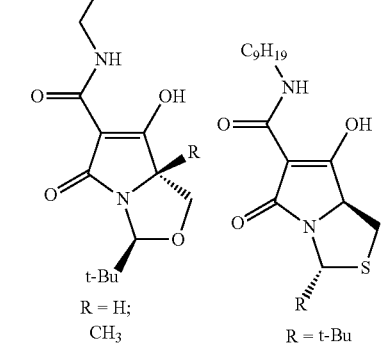
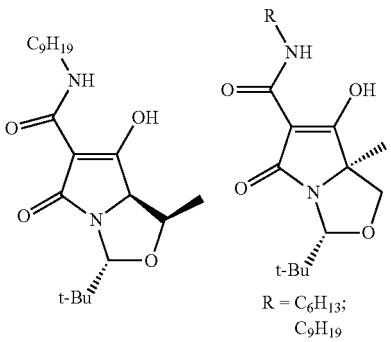

-continued
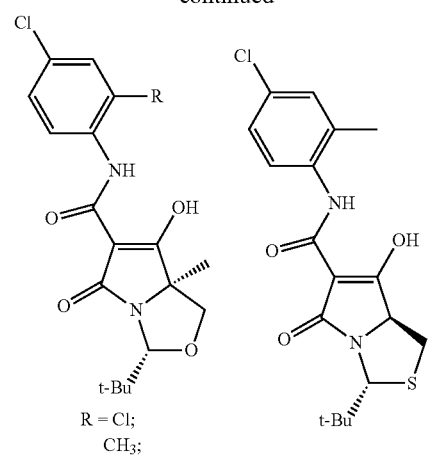
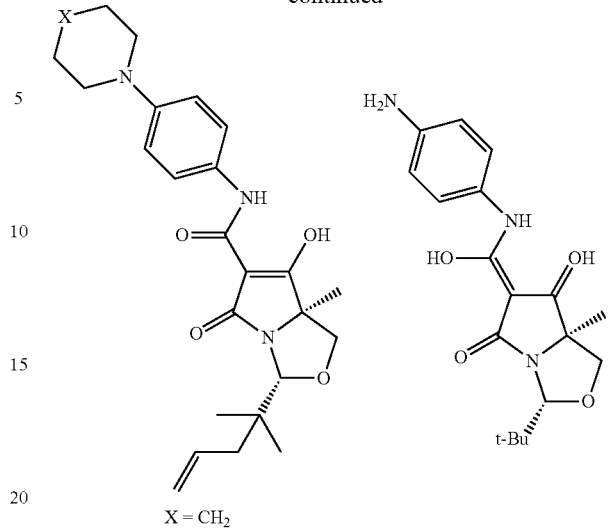
X = CH₂
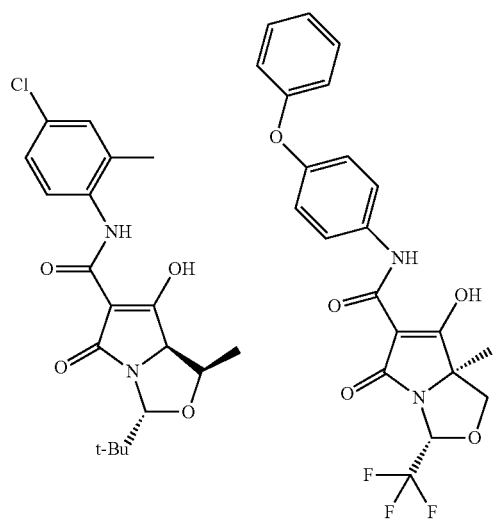
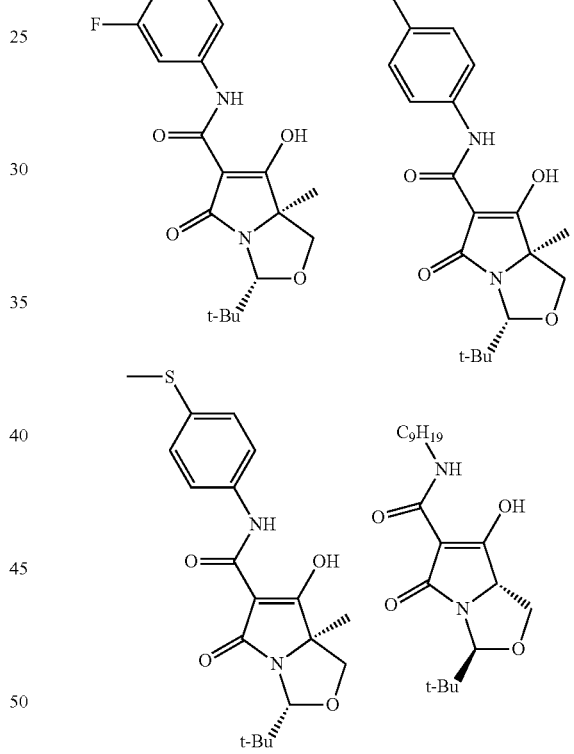
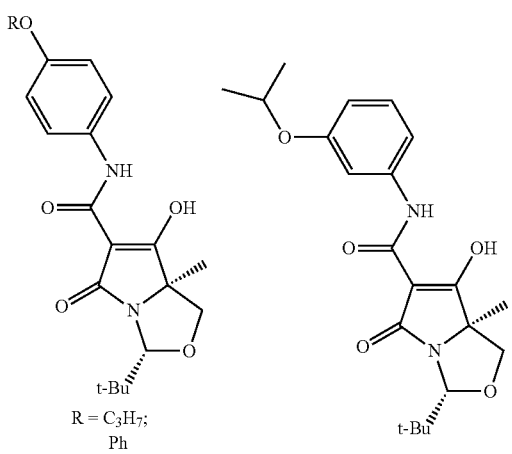
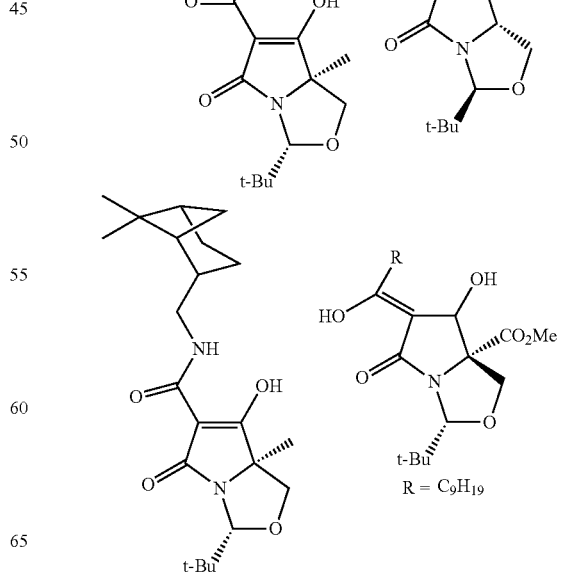

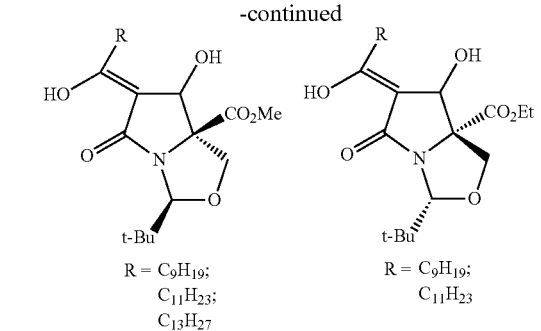
R = C9H19;
C11H23;
C13H27
R = C9H19;
C11H23
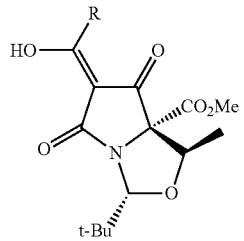
R = C9H19;
C11H23;
C12H25;
C13H27;
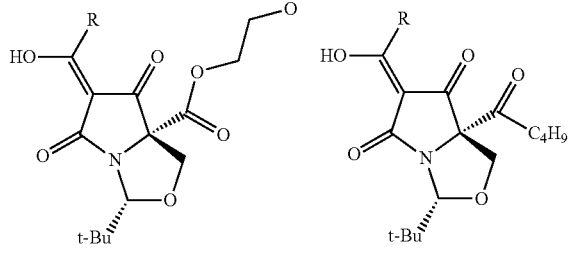
R = C9H19;
C11H23;
R = C7H15;
C9H19
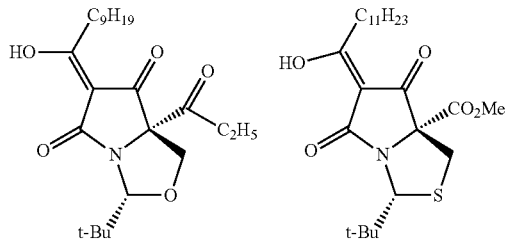
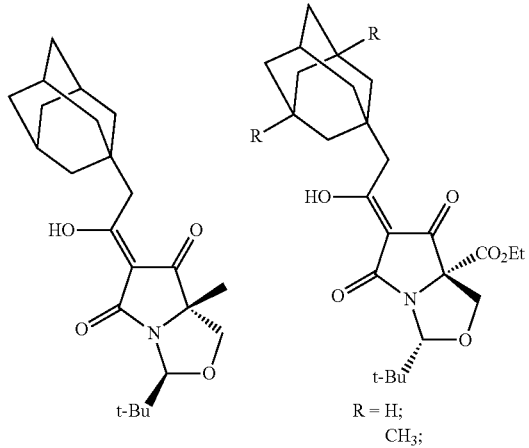
R = H;
CH3;
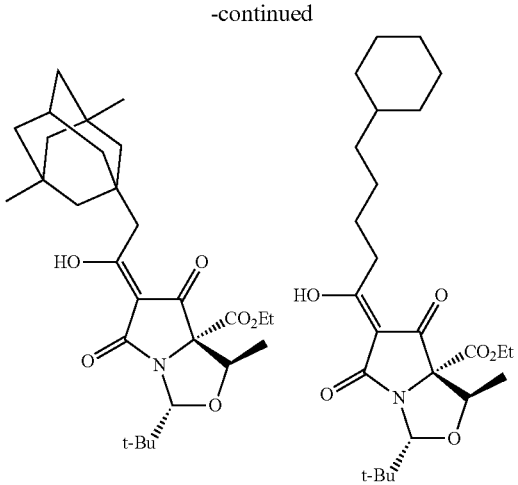
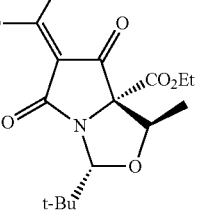
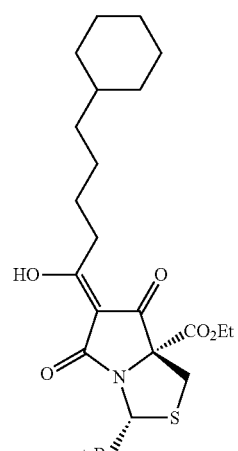
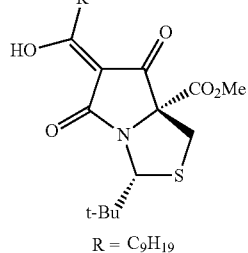
R = C9H19
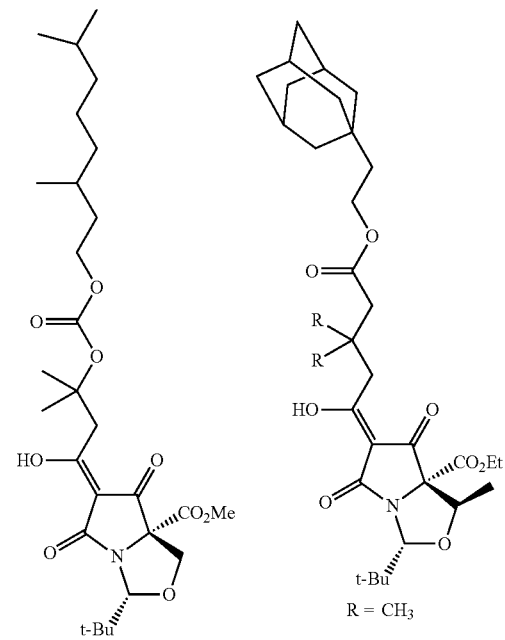
R = CH3

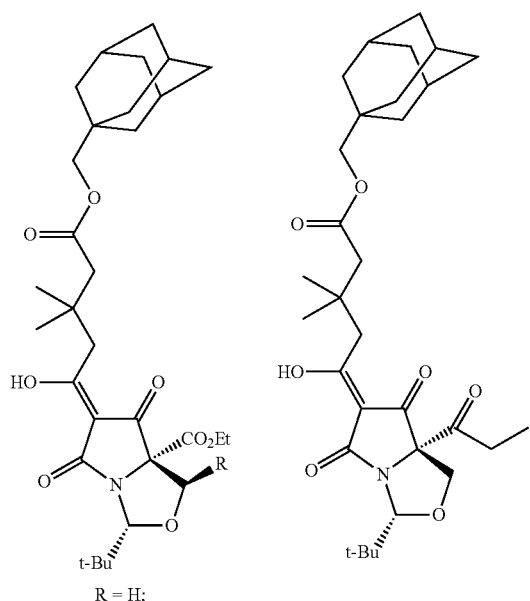
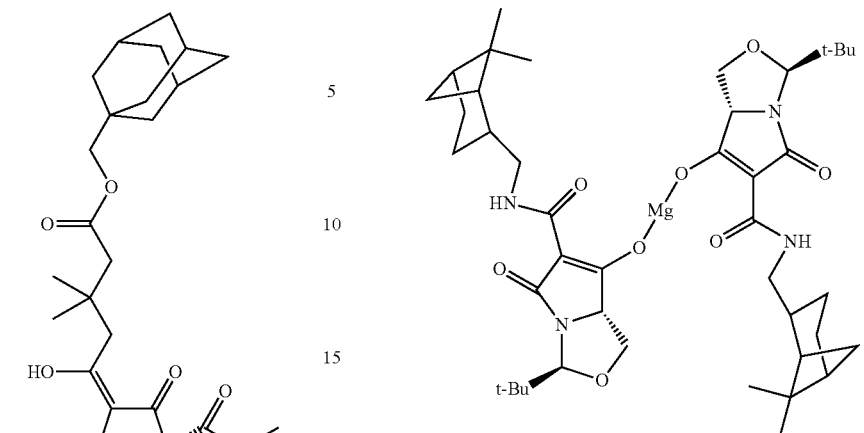
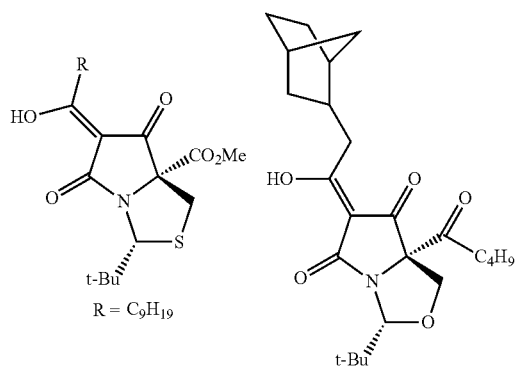
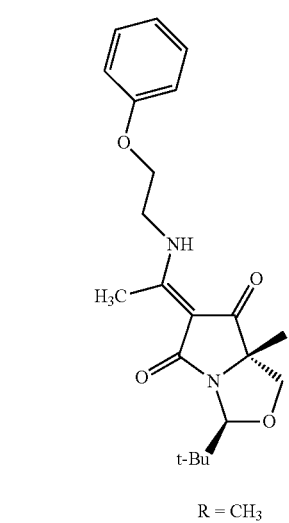 [SMILES: C/C(NCCOc1ccccc1)=C1\C(=O)N2[C@H](C(C)(C)C)OC[C@@]2(C)C1=O]
Preferably, the compound is selected from at least one of the following:
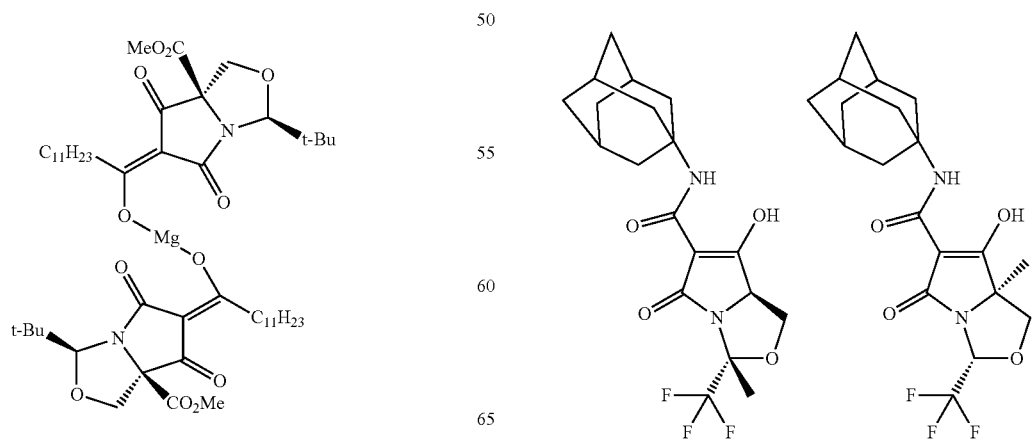

-continued
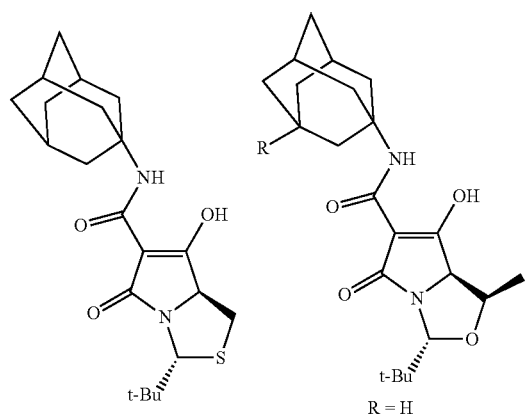
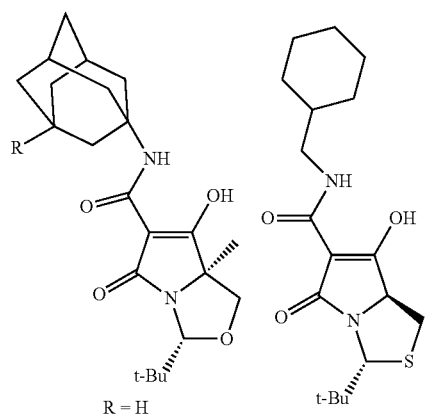
R = H
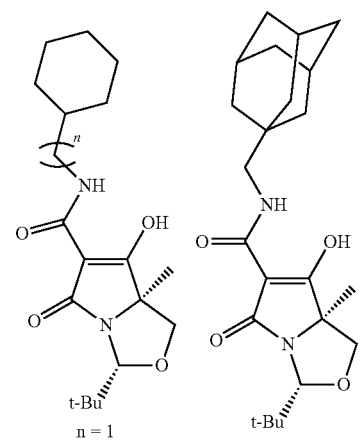
n = 1
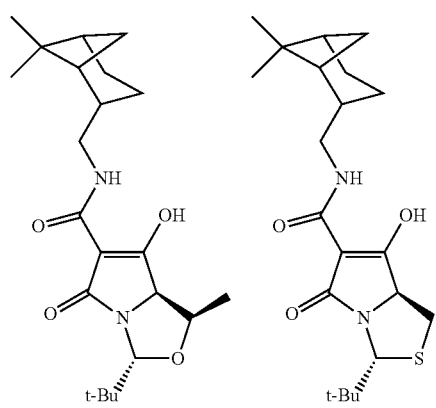
-continued
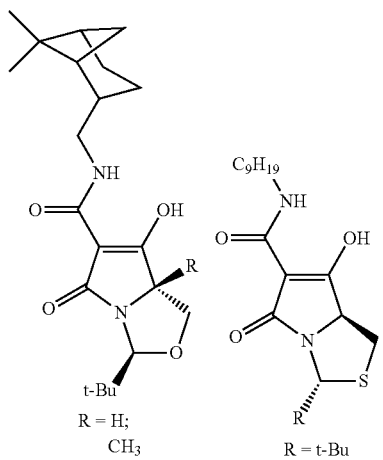
R = H;
CH₃
R = t-Bu
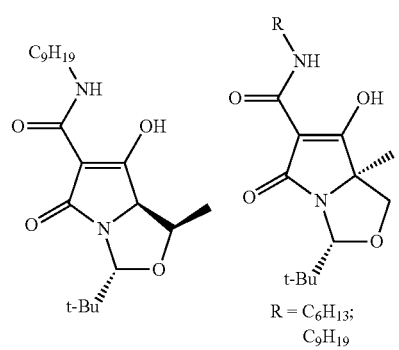
R = C₆H₁₃;
C₉H₁₉
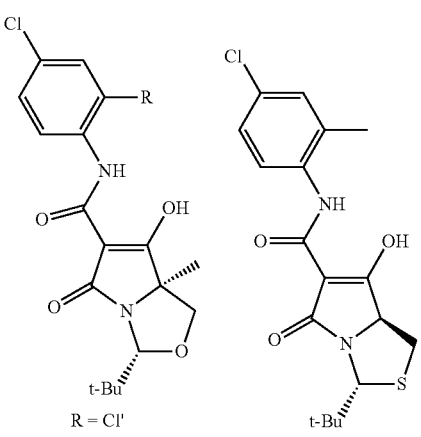
R = Cl;
CH₃;
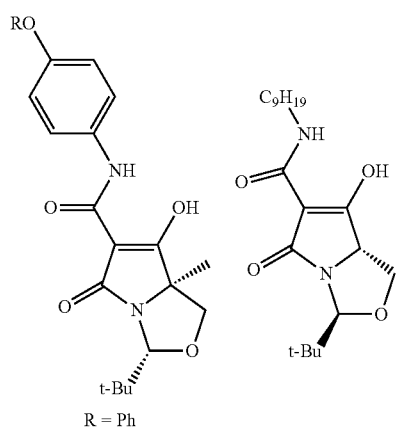
R = Ph

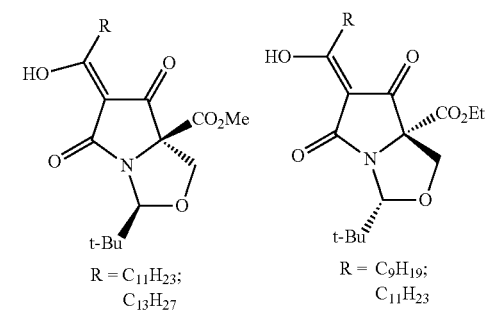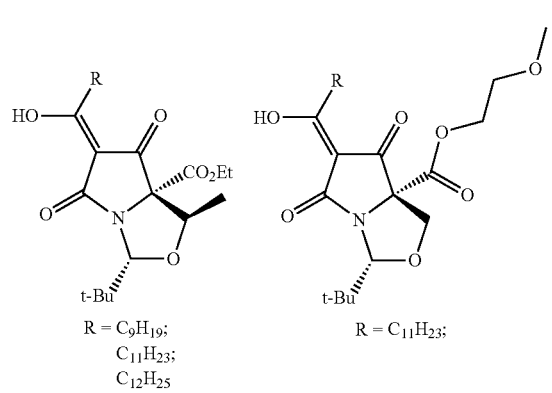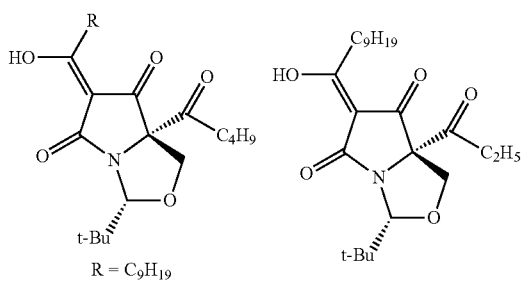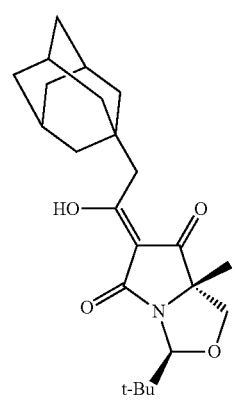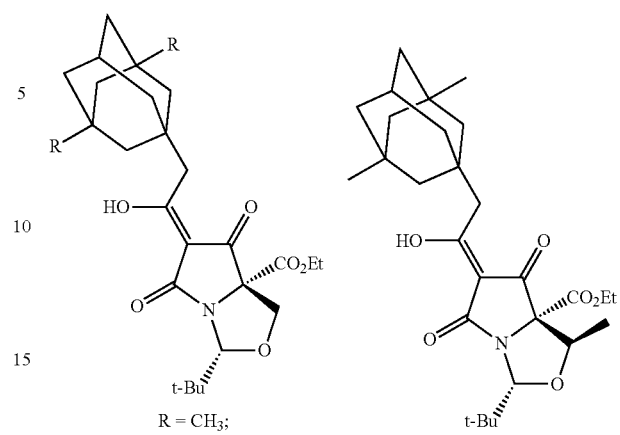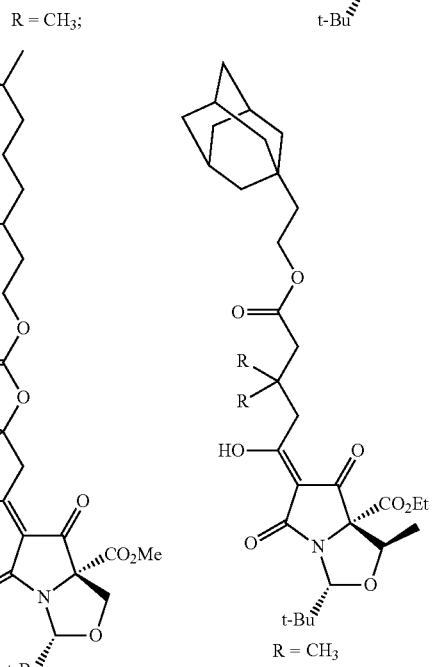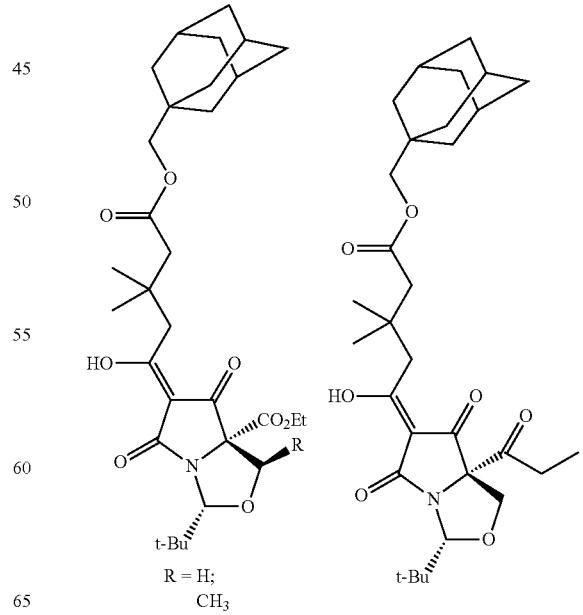

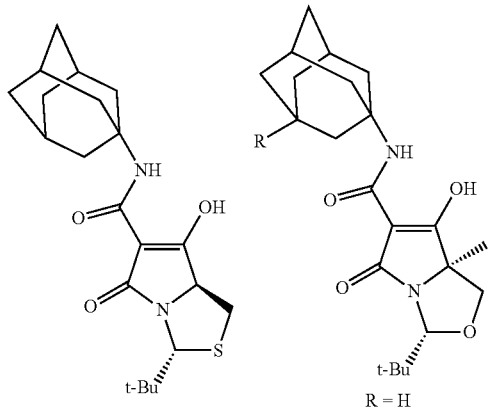
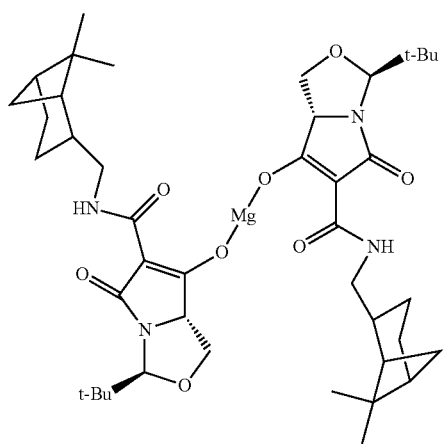
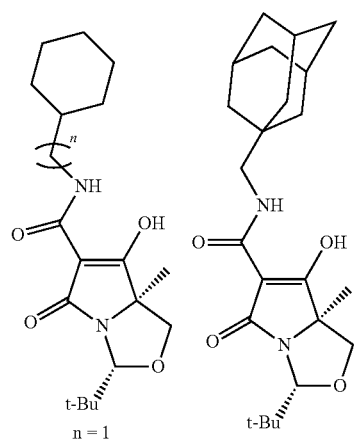
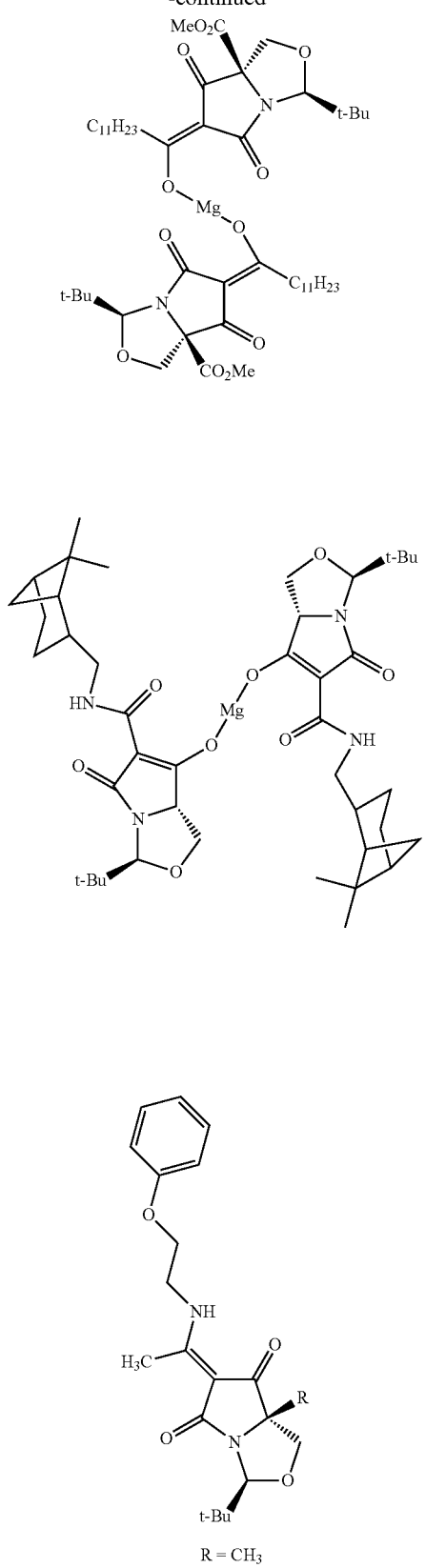
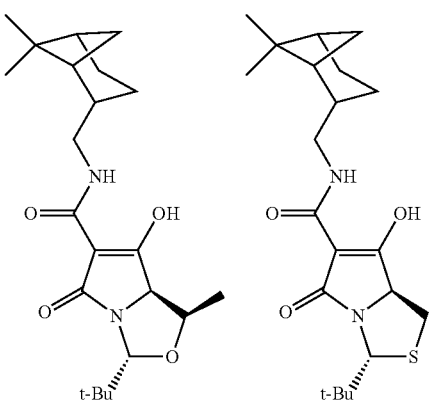
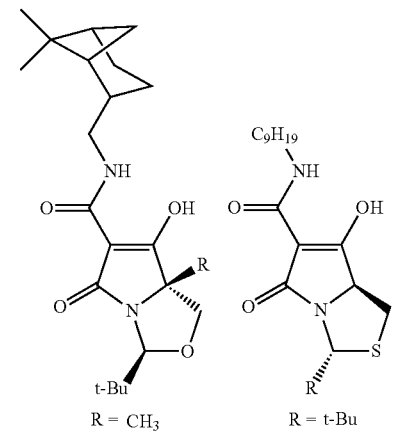
More preferably, the compound is selected from at least one of the following:

-continued
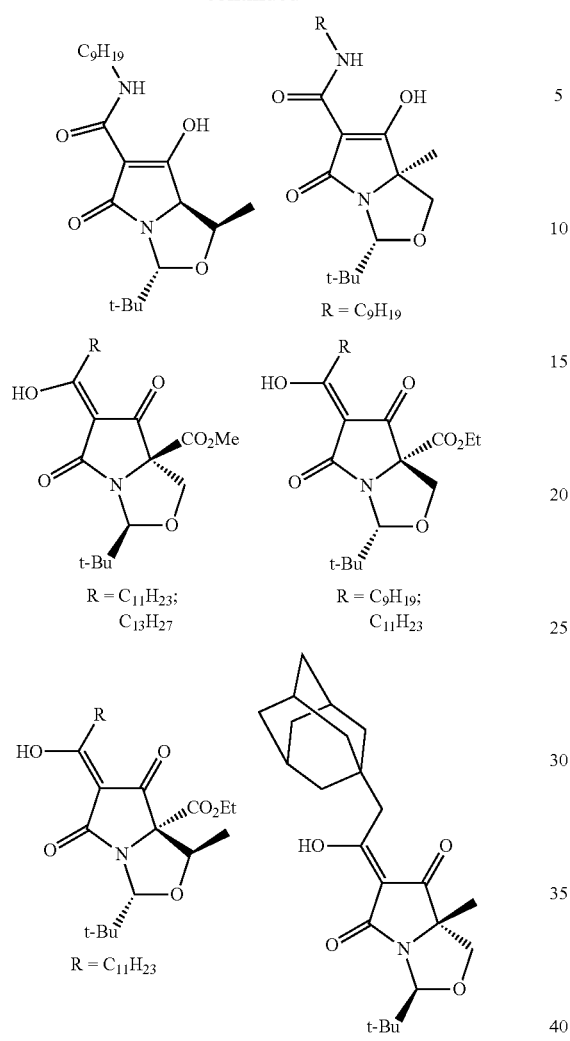
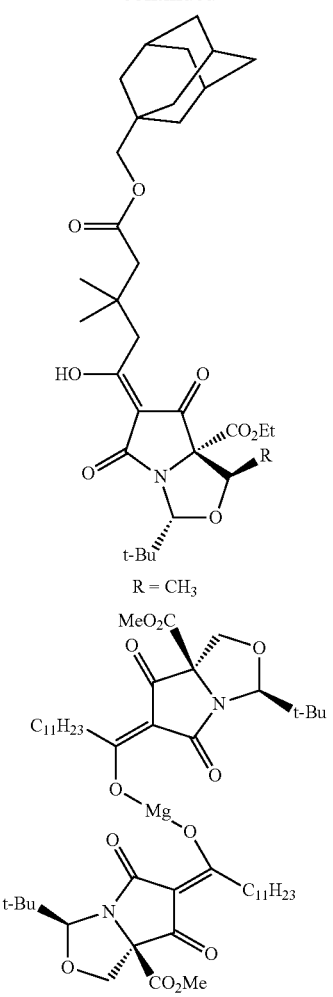
Other examples include
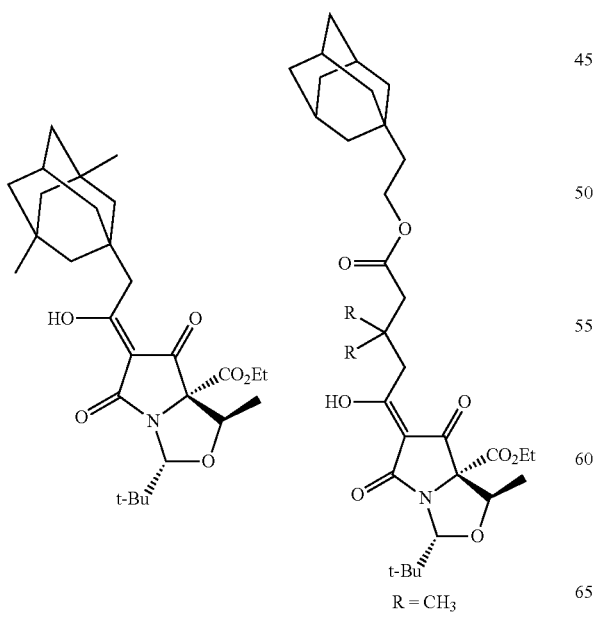
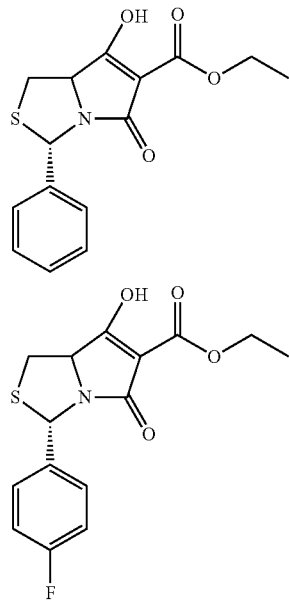

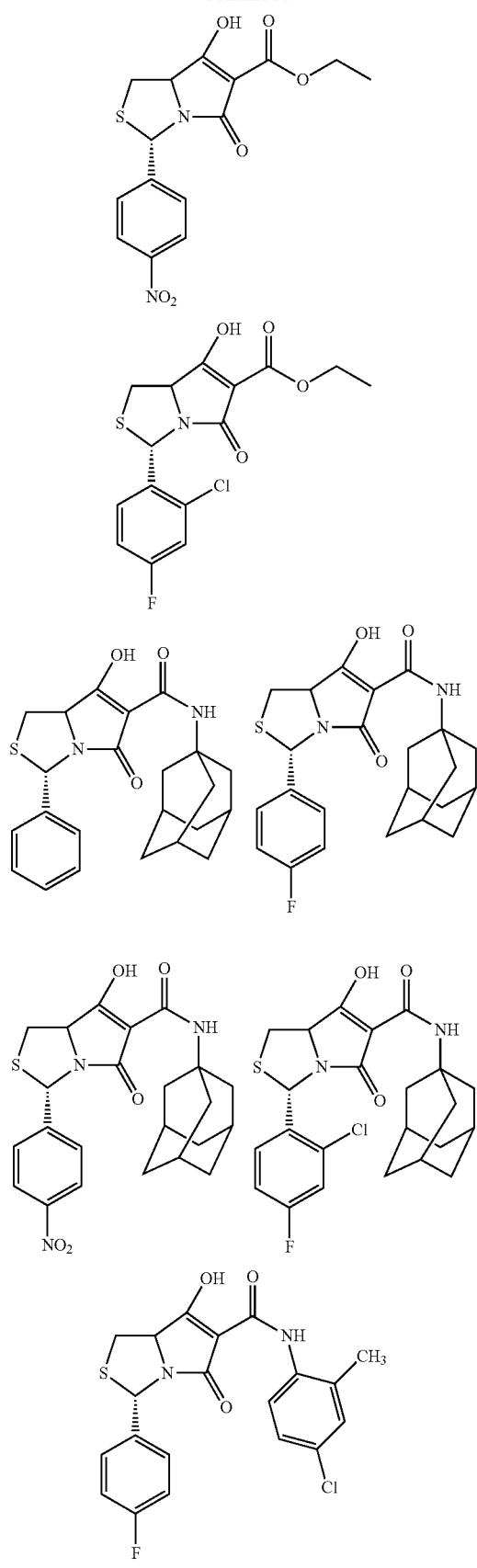

-continued

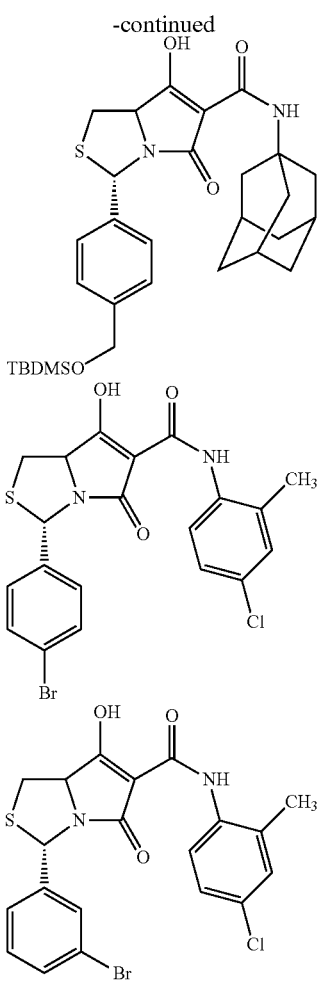

In one embodiment, the following compounds are excluded:

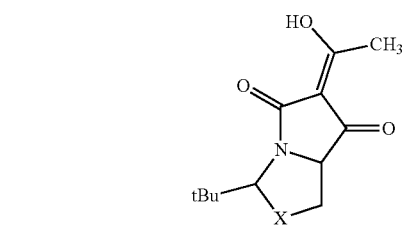

where X is O or S

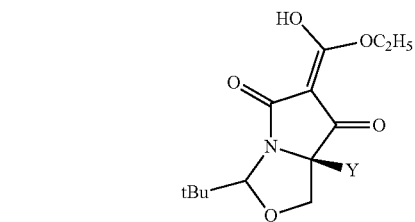

where Y is H or CH$_3$

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

In one aspect, the present invention provides method of synthesising a compound of the Formula II, which comprises:

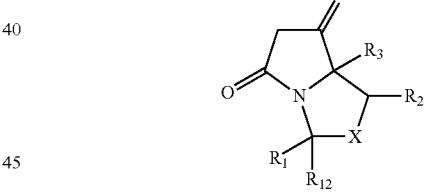

reacting a compound of the formula III with a carboxylic acid of the formula R$_7$CO$_2$H; or reacting a compound of the formula III with i) a carboxylic acid of the formula R$_7$CO$_2$H or ii) an acid chloride of the formula R$_7$COCl, to form a compound of the formula IV below, where R is a hydrocarbyl group,

IV

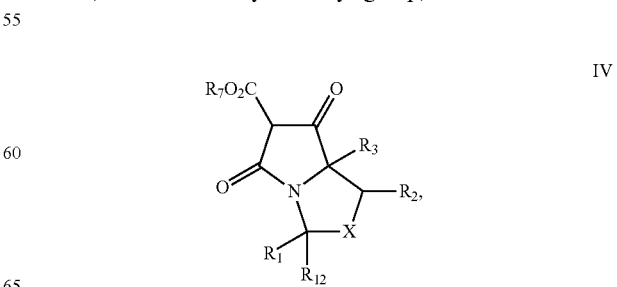

and reacting the compound of the Formula IV with a base (preferably 4-dimethylaminopyridine or triethylamine) to convert the O-acyl derivative to the corresponding C-acyl derivative.

In another aspect, the present invention also provides a method of synthesising a compound of the Formula I, wherein Y is a $C_1$ to $C_{10}$ alkyl, which comprises reacting a compound of Formula II with an amine of the formula $R_4R_5NH$.

In yet another aspect, the present invention provides a method of synthesising a compound of the Formula Ia, which comprises

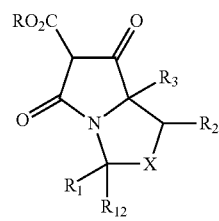

with an amine of the formula $R_4R_5NH$, with the proviso that, where compound III is reacted with $R_5NCO$, $R_4$ is H.

The compound of Formula IV may be formed by acylating a compound of Formula III, preferably with $R_7OC(O)Cl$.

In one embodiment, the following reagents and/or reaction conditions are used in the synthesis of compounds of the invention:

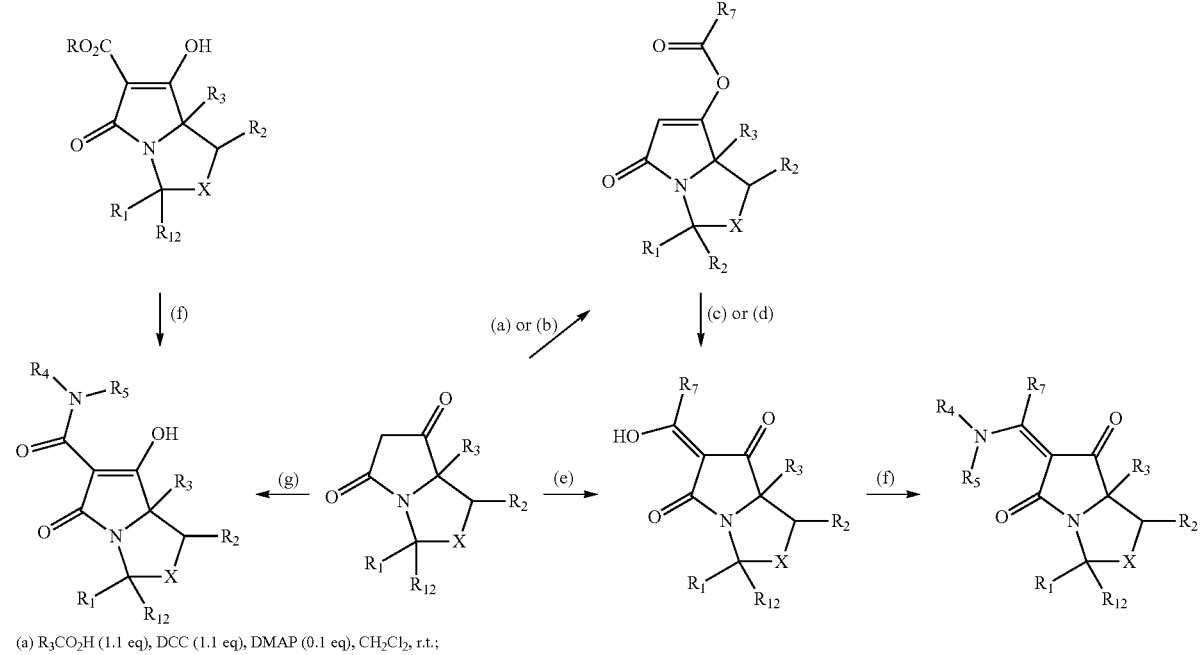

(a) $R_3CO_2H$ (1.1 eq), DCC (1.1 eq), DMAP (0.1 eq), $CH_2Cl_2$, r.t.;
(b) $R_3COCl$ (1.1 eq), triethylamine (1.2 eq), $CH_2Cl_2$, r.t.;
(c) $(CH_3)_2C(OH)CN$ (0.5 eq), triethylamine (2.0 eq), $CH_3CN$, r.t.;
(d) DMAP (1.3 eq), $CH_2Cl_2$, r.t.;
(e) $R_3CO_2H$ (1.1 eq), DCC (1.1 eq), DMAP (1.3 eq), $CH_2Cl_2$, r.t.;
(f) Amine (1,1 eq), toluene, reflux.
(g) RNCO (1.1 eq), DMAP (1.1 eq), $CH_2Cl_2$, r.t.

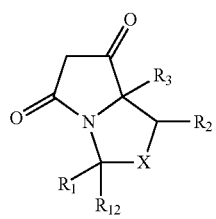

a) reacting a compound of the formula III with a compound of the formula $R_5NCO$, or reacting a compound of the formula IV', where R is a hydrocarbyl group or $R_7$:

Representative procedures for steps (e), (f) and (g) are given, by way of example, below.

Step (e): Acylation of tetramates. 3-Acyltetramic acids were prepared by reported method (Jeong, Y.-C. & Moloney, M. G. Synthesis of and tautomerism in 3-acyltetramic acids. J. Org. Chem. 76, 1342-1354 (2011)), and the direct acylation of tetramic acid with carboxylic acid was achieved by using 1.1 equivalent of N,N'-dicyclohexylcarbodiimide (DCC) and 1.2 equivalent of 4-(dimethylamino)pyridine (DMAP).

Step (f) for formation of 3-enamine tetramic acids. 3-Enamine tetramic acids were prepared from corresponding 3-acyltetramic acids and amine by using similar method with the synthesis of 3-carboxamide tetramic acids. (Ostrowska, K. et al. Monatshefte für Chemie 1999, 130, 555-562.)

Step (f) for formation of 3-Carboxamide tetramates. 3-Carboxamide tetramic acids were prepared by direct amine exchange of corresponding ester tetramic acid under refluxing conditions in toluene using the literature procedure (Folkes, A. et al. *Bioorg. Med. Chem. Lett.* 2002, 12, 1063-1066.), providing access to a range of amides in good to excellent yield (20-90%).

Step (g) for formation of 3-carboxamide tetramates. 3-Carboxamide tetramic acids could be also prepared from tetramic acid with 1.1 equivalents of isocyanate in presence of 1.1 equivalents of DMAP.

The synthetic sequence for forming a compound of the Formula III is known in the art. Reference may be made to "Control of chemoselectivity in Dieckmann ring closures leading to tetramic acids", Y.-C. Jeong, M. Anwar, T. Minh Nguyen, B. Song Wei Tan, C. Li Lin Chai and M. G. Moloney, Org. Biomol. Chem., 2011, 9 (19), 6663-6669; "Synthesis of and tautomerism in 3-acyltetramic acids, Y.-C. Jeong, and M. G. Moloney, J. Org. Chem., 2011, 76, 1342-1354; "Enantioselective Synthesis of Tetramic Acids and Lactams from Threonine and their Antibiotic Activity", M. Anwar and M. G. Moloney, Tetrahedron: Asymmetry, 2010, 21, 1758-1770; "Chemoselective Dieckmann Cyclisations Leading to Enantiopure Highly Functionalised Tetramic Acid Derivatives", M. D. Andrews, A. G. Brewster, J. Chuhan, K. M. Crapnell, A. J. Ibbett, M. G. Moloney, C. K. Prout, and D. J. Watkin, J. Chem. Soc., Perkin Trans 1, 1998, 223-235.). An example of a suitable synthetic sequence for forming a compound falling within Formula III is described below. In the sequence below, steps l and m have not been reported. These are described, by way of example, in paragraphs below.

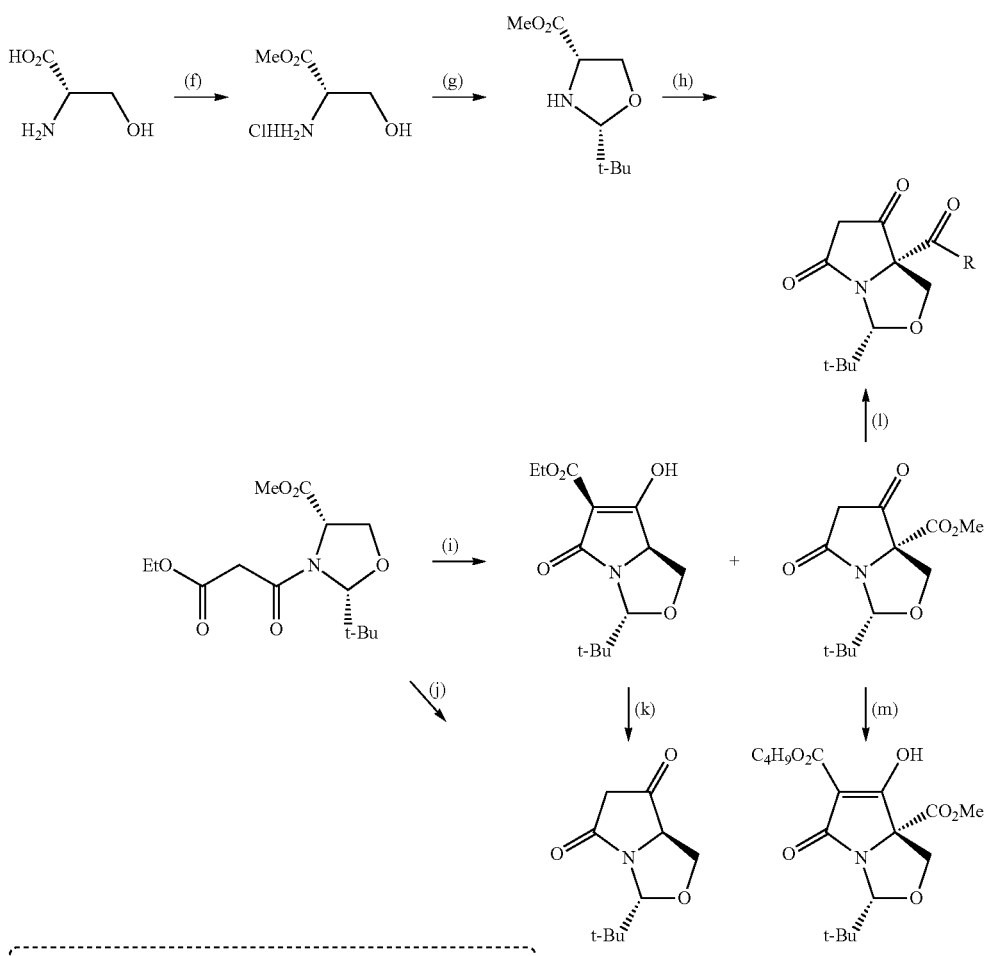

Scheme 1

(f) SOCl₂, CH₃OH, 40 C.
(g) Me₃CCHO (1.1 eq), TEA (1.1 eq), petrol, reflux,
(h) mono-Ethylmalonate (1.1 eq), DCC (1.1 eq), DMAP (0.1 eq), CH₂Cl₂, r.t.
(i) KtBuO (1.1 eq), dry BuOH, reflux,
(j) KtBuO (2.2 eq), wet BuOH, reflux,
(k) wet CH₃CN, reflux,
(l) RMgBr (4.0 eq), THF, -78 C.,
(m) Butyl chloroformate (1.2 eq), DMAP (2.2 eq), CH₂Cl₂, r.t.

Step (l): Addition of Grignard Reagents

Keto derivatives were obtained from the starting ester template by reaction with 5 equivalents of ethyllithium or of n-butyllithium. Due to the existence of the acidic proton at 3-position, excess amounts of the alkyllithium were required.

Step (m): Acylation with Chloroformates

Diester derivatives were obtained by using 1.2 equivalents of butyl chloroformate and 2.2 equivalents of DMAP in $CH_2Cl_2$ with the starting tetramate under room temperature.

Example 1

The following compounds were tested:

Compound (+/-) 2A

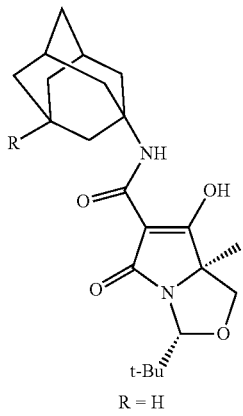

R = H

Compound (+/-) 2E

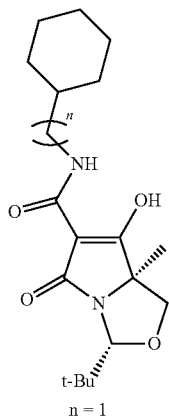

n = 1

Compound (+/-) 6C

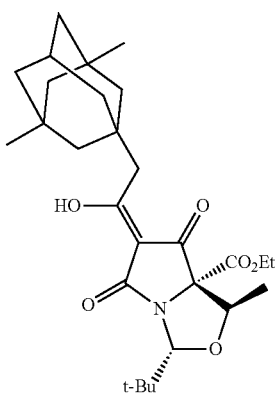

Compound (+/-) 6G

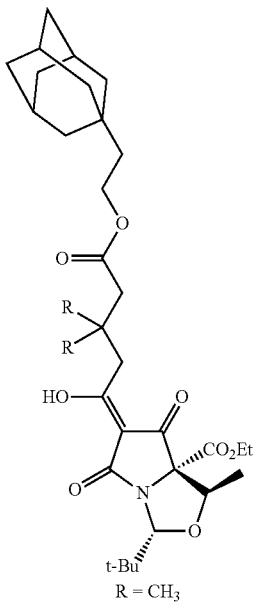

R = $CH_3$

MIC determination (bacteria); MICs were determined based on Clinical and Laboratory Standards Institute (CLSI) methodology (Methods for dilution antimicrobial susceptibility tests for bacteria that grow aerobically; Approved Standard—seventh edition. 2006, M7-A7, CLSI, Wayne Pa.) by a 2-fold broth dilution technique in Mueller Hinton (pH7.4 Biorad). For *S. pneumoniae*, the medium was supplemented with 2.5% laked horse blood. For *H. influenzae*, the medium was haemophilus test medium (H.T.M.). Overnight cultures were diluted to obtain the final inoculum of 105 cfu/well. Incubation was 37° C. overnight in ambient air. The MIC was defined as the lowest concentration which inhibited all visual growth and expressed in µg/ml. For each bacterial species, all of the molecules were tested in the same experiment in order to give a head-to-head comparison. The results are shown in Table 2 below:

MIC determination (fungus); MICs were determined for the antifungus by microdilution methods using RPMI 1640 medium buffered with morpholinopropanesulfonic acid (MOPS) and supplemented with L-glutamine as described by CLSI procedures (M27-A method) (Reference method for broth dilution antifungal susceptibility testing of yeasts; Approved standard—third edition. 2006, M27-A2, CLSI, Wayne Pa.). After incubation for 24-48 hours at 35° C., the lowest concentration of drug which produced 80% reduction in visible growth compared with control was considered as the MIC. The results are shown in Table 2 below.

The pharmacological properties of these derivatives were also determined and the results are shown in Table 1 below. These properties can be determined according to techniques that are well known in the art.

TABLE 1

Pharmacological properties of selected tetramic acids[a,c]

| | RNA IC$_{50}$, μM | UPP IC$_{50}$, μM | DEP IC$_{50}$, μM | RBC IC$_{50}$, μM | CAN MIC, μg/ml | HEK LD$_{50}$, μM | PMB LD$_{50}$, μM | SOL μM | PPB % |
|---|---|---|---|---|---|---|---|---|---|
| (±)-2A | 17 | 0.38 | 10.8 | >100 | >32 | 30.3 | 30.3 | 75-150 | —[c] |
| (±)-2E | 31 | 0.68 | 84.3 | >100 | >32 | 90.9 | 90.9 | >300 | 96.6 |
| 6C | 4.0 | 3.2 | >100 | >100 | >32 | 90.9 | >90.9 | >300 | 99.8 |
| 6G | 2.4 | 1.9 | >100 | >100 | >32 | 10.1 | >90.9 | >300 | —[c] |

[a]abbreviation; RNA; In vitro activity against *E. Coli* RNAP, UPP; In vitro activity against *S. pneumonia* UPPS, DEP; In vitro activity in depolarization of *S. aureus* membrane, RBC; In vitro mammalian red blood cell membrane lysis activity,CAN; In vitro antifungal activity against *Candida albicans*, HEK; in vitro toxicities against human embryonic kidney 293 cells, PMB; in vitro toxicities human peripheral blood cells, SOL; aqueous solubility at pH 7.4 (water with 2% DMSO), PPB; % ratio of plasma protein binding. [c]Not determined.

TABLE 2

In vitro antibiotic activity (MIC, μg/mL) of tetramic acids[a]

| | S1 | S26 | S4 | S2 | E1 | E2 | P1 | P9 | P9B | H3 | H4 |
|---|---|---|---|---|---|---|---|---|---|---|---|
| (±)-2A | 1 | 2 | 1 | 1 | 1 | 1 | 1 | 1 | 1 | 2 | 1 |
| (±)-2E | 4 | 4 | 4 | 2 | 2 | 1 | 2 | 1 | 1 | 4 | 0.12 |
| 6C | 2 | 2 | 2 | 1 | 2 | 1 | 0.5 | 0.5 | 1 | 64 | 0.25 |
| 6G | 0.5 | 1 | 1 | 0.5 | 1 | 0.5 | 2 | 1 | 4 | >64 | 2 |

[a]abbreviation; S1; *S. aureus* 1, ATCC13709 in vivo (methicillin sensitive), S26; *S. aureus* 26, ATCC25923 (vancomycin susceptible), S4; *S. aureus* 4, Oxford, S2; *S. aureus* 2, (MRSA in vivo), E1; *E. faecalis* 1, ATCC29212 VanS (vancomycin susceptible), E2; *E. faecium* 1, VanA (vancomycin resistant), P1; *S. pneumonia* 1, ATCC49619 (erythromycin susceptible), P9; *S. pneumonia* 9, (multi-drug resistant), P9B; *S. pneumonia* 9 in presence of 2.5% horse blood, H3; *H. influenzae* 3, ATCC31517 MMSA, H4; *H. influenzae* 4, LS2 Efflux ko, b; All analogues are inactive (MIC > 64 μg/ml) against *E. coli* 1, ATCC25922 (non pathogenic strain), *E. coli* 50, Ec49 No Efflux and *P. aeruginosa* 1, ATCC27853.

Example 2

Various compounds illustrative of the compounds of the present invention were synthesised and tested for their bioactivity. Microbiological assays were performed by the hole-plate method with the test organism *Staphylococcus aureus* N.C.T.C. 6571 or *E. coli* X580. Solutions (100 μl) of the compounds to be tested (4 mg/ml) were loaded into wells in bioassay plates, and incubated overnight at 37° C. The diameters of the resultant inhibition zones were measured.

The results are shown in the tables below.

| Compound | Bioactivity (mm) | | LogP | Polar Surface Area (PSA) | Molecular Surface Area (MSA) | % PSA/MSA | % Yield |
|---|---|---|---|---|---|---|---|
| | *S. aureus* (4 mg/ml) | *E. coli* (4 mg/ml) | | | | | |
| (structure: ethyl ester tetramic acid with thiazolidine bearing 4-nitrophenyl) | 16 | X | 1.73 | 112.66 | 431.52 | 26.11 | 80 |

-continued

| Compound | | | | | LogP | Polar Surface Area (PSA) | Molecular Surface Area (MSA) | % PSA/MSA | % Yield |
|---|---|---|---|---|---|---|---|---|---|
| (thiazolidine with COOMe, N-CO-CH2-COOEt, 2-(2-Cl-4-F-phenyl)) | X | 16 | | | 2.68 | 72.91 | 500.64 | 14.56 | 97 |
| (pyrrolo-thiazole with OH, COOEt, 2-Cl-4-F-phenyl) | 18 | X | | | 2.54 | 66.84 | 414.75 | 16.12 | 84 |

| | Bioactivity (mm) | | | | | | | | |
|---|---|---|---|---|---|---|---|---|---|
| | S. aureus | | E. coli | | | Polar Surface | Molecular Surface | | |
| | 0.01 mg/ml | 0.001 mg/ml | 0.01 mg/ml | 0.001 mg/ml | LogP | Area (PSA) | Area (MSA) | % PSA/MSA | % Yield |
| Compound | | | | | | | | | |
| (pyrrolo-thiazole with OH, CONH-adamantyl, phenyl) | 22 | X | 15 | 15 | 1.23 | 69.64 | 545.16 | 12.8 | 38 (from crude) |
| (pyrrolo-thiazole with OH, CONH-adamantyl, 4-F-phenyl) | 27 | 21 | 14 | X | 1.05 | 69.64 | 552.66 | 12.6 | 56 |

-continued

| Compound | | | | | | | | | |
|---|---|---|---|---|---|---|---|---|---|
| (structure: pyrrolothiazole with OH, C(=O)NH-adamantyl, 4-nitrophenyl) | 25 | 19 | 14 | X | 0.72 | 115.46 | 584.98 | 19.7 | 35 (from crude) |
| (structure: pyrrolothiazole with OH, C(=O)NH-adamantyl, 2-chloro-4-fluorophenyl) | 25 | 21 | 14 | X | 1.37 | 69.64 | 567.97 | 12.3 | 60 |

| Compound | Bioactivity (mm) | | LogP | Polar Surface Area (PSA) | Molecular Surface Area (MSA) | % PSA/MSA | % Yield |
|---|---|---|---|---|---|---|---|
| | *E. coli* (4 mg/ml) | *S. aureus* (4 mg/ml) | | | | | |
| (structure: pyrrolothiazole ethyl ester with 3-bromophenyl) | XX | 2.0 Cm | 2.56 | 66.84 | 410.79 | 16.27 | 78 |
| (structure: pyrrolothiazole ethyl ester with 4-bromophenyl) | XX | 1.7 Cm | 2.56 | 66.84 | 410.86 | 16.27 | 82 |

-continued
| | | | | | | | |
|---|---|---|---|---|---|---|---|
| 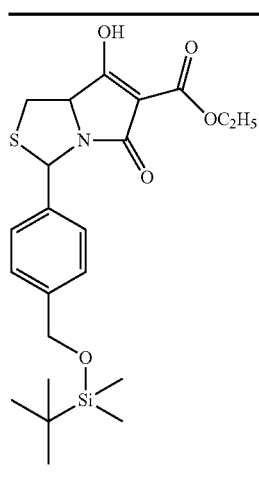 | XX | 2.3 Cm | 3.79 | 76.07 | 668.64 | 11.38 | 72 |
| Compound | Bioactivity (mm) | | | | LogP | Polar Surface Area (PSA) | Molecular Surface Area (MSA) | % PSA/MSA | % Yield |
|---|---|---|---|---|---|---|---|---|---|
| | E. coli | | S. aureus | | | | | | |
| | 0.5 mg/ml | 0.25 mg/ml | 0.5 mg/ml | 0.25 mg/ml | | | | | |
| 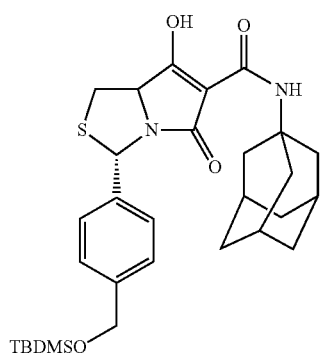 [SMILES: CC(C)(C)[Si](C)(C)OCc1ccc([C@@H]2SCC3C(O)=C(C(=O)NC45CC6CC(CC(C6)C4)C5)C(=O)N32)cc1] | X | X | 13 | 12 47 | 2.39 | 78.87 | 821.82 | 9.59 | 28 (from crude) |
|  | X | X | 26 | 25 | 4.38 | 69.64 | 503.62 | 13.82 | 41 (from crude) |

The invention claimed is:

1. A compound of the formula I below:

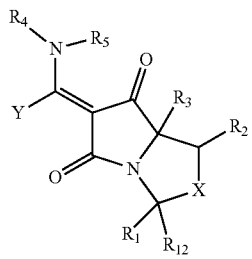

Formula I wherein:
X is O, S or SO$_2$,
Y is OH or C$_1$ to C$_{10}$ alkyl,
R$_1$, R$_2$ and R$_4$ are each independently selected from H and C$_1$ to C$_6$ alkyl,
R$_3$ is selected from a functional group selected from H, C$_1$ to C$_6$ alkyl, and a carbonyl-containing group,
R$_{12}$ is H, alkenyl, aryl, trihaloalkyl and C$_1$ to C$_6$ alkyl,
R$_5$ is a group of the formula L$_1$-L$_2$-R$_6$ or L$_2$-L$_1$-R$_6$,
where L$_1$ is a linker of the formula —[CR$_8$R$_9$]$_n$—, where n is an integer of from 0 to 12, and R$_8$ and R$_9$ are each independently selected from H or C$_1$ to C$_2$ alkyl, and
where L$_2$ is absent or a linker that is selected from O, S, SO, SO$_2$, N(R'), C(O), C(O)O, OC(O), [O(CR'$_2$)$_r$]$_s$, [(CR'$_2$)$_r$O]$_s$, CH(OR'), C(O)N(R'), N(R')C(O), N(R')C(O)N(R'), SO$_2$N(R') or N(R')SO$_2$ where R' and R" are each independently selected from hydrogen and a C$_1$ to C$_2$ alkyl, and where r is 1 or 2 and s is 1 to 4, and
where R$_6$ is selected from OR$^{13}$, heterocyclic and C$_1$ to C$_{25}$ hydrocarbyl group, wherein R$^{13}$ is a C$_1$ to C$_6$ alkyl, and said heterocyclic and hydrocarbyl group is optionally substituted with at least one functional group selected from alkenyl, alkyl, aryl, halo, trihaloalkyl, alcohol, keto, S(O)R$^{13}$, sulfonyl, thio-alcohol, ester, thioester, ether, thioether, amide, thioamide, urea, thiourea, =O, =S, amine and heterocyclic group;
and tautomers, salts, and solvates thereof.

2. The compound as claimed in claim 1, which has the formula:

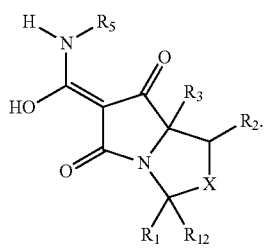

Formula Ia

3. The compound as claimed in claim 1, wherein n is 0 or 1 and L$_2$ is absent.

4. The compound as claimed in claim 1, where R$_6$ is an alkyl that is a bridged ring system.

5. The compound as claimed in claim 1, wherein R$_6$ is an alkyl group selected from adamantyl, myrtanyl, cyclohexyl and a C$_6$ to C$_{19}$ non-cyclic aliphatic alkyl group.

6. The compound as claimed in claim 1, wherein R$_6$ is a phenyl group that is optionally substituted with at least one functional group selected from alkyl, aryl, halo, trihaloalkyl, alcohol, thio-alcohol, ester, thioester, ether, thioether, amide, thioamide, urea, thiourea and heterocyclic group.

7. The compound as claimed in claim 6, wherein the phenyl group is substituted with a heterocyclic group selected from a piperidine and morpholine group, or where the phenyl group is fused to an aromatic heterocyclic ring.

8. The compound as claimed in claim 7, where the aromatic heterocyclic ring is a pyrrole ring.

9. The compound as claimed in claim 1, wherein R$_3$ is selected from H, methyl, C(O)R$_{11}$, and C(O)O[CR$_8$R$_9$]$_n$OR$_{11}$, where R$_{11}$ is a C$_1$ to C$_4$ alkyl group.

10. The compound as claimed in claim 1, wherein R$_1$ is selected from H, methyl, ethyl, n-propyl, i-propyl, n-butyl, s-butyl, i-butyl and t-butyl.

11. The compound as claimed in claim 1, having the formula:

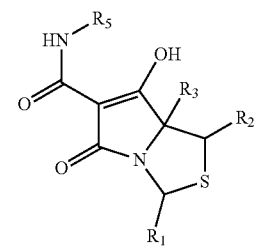

wherein R$_5$ is selected from 1-adamantyl and CH$_2$—C$_6$H$_5$, or

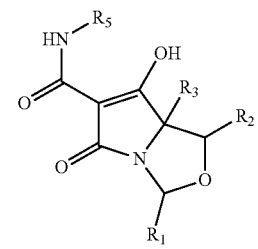

wherein R$_5$ is CH$_2$—C$_6$H$_5$.

12. The compound as claimed in claim 1, selected from

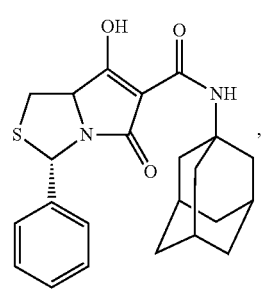

51
-continued
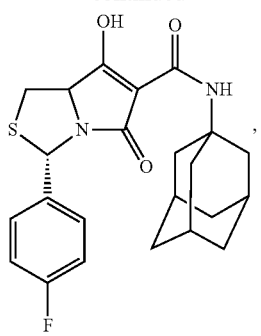
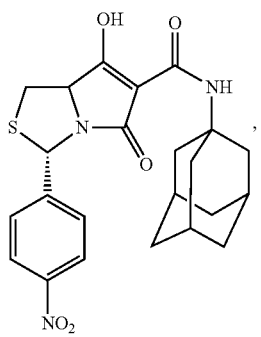
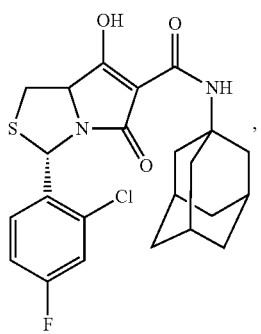
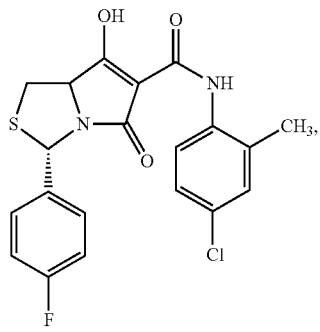
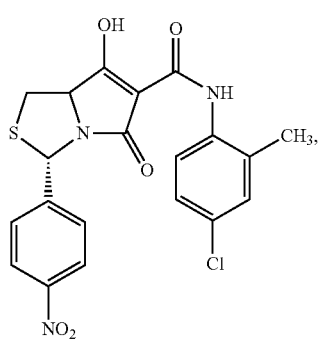
52
-continued
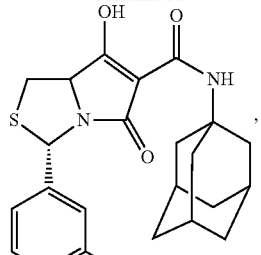
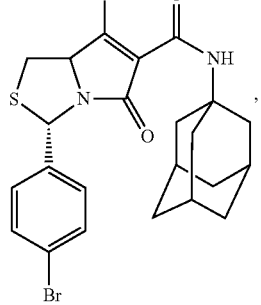
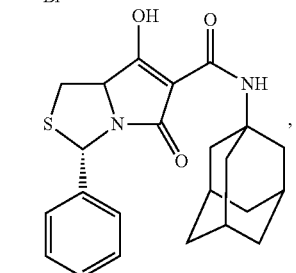
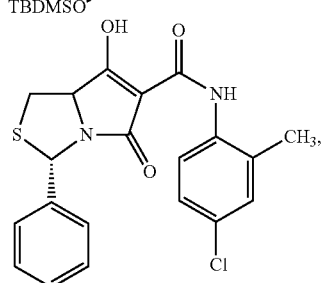
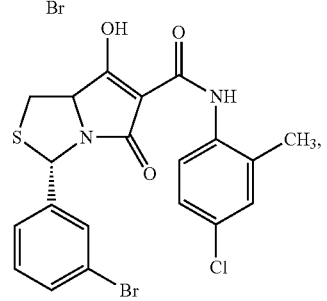
and tautomers, salts, and solvates thereof.
13. The compound as claimed in claim 1, where the salts are pharmaceutically acceptable salts.
14. A compound as claimed in claim 1 for use in a medicament for treating a topical microbial infection.

15. An antibacterial composition comprising a compound as claimed in claim 1 or a pharmaceutically acceptable salt thereof.

16. The composition as claimed in claim 15, which is a topical antimicrobial composition.

17. A method of using a compound as claimed in claim 1 or a pharmaceutically acceptable salt thereof as an antimicrobial agent, the method comprising adding the compound or the pharmaceutically acceptable salt thereof to a composition or applying the compound or the pharmaceutically acceptable salt thereof to an object.

18. The method as claimed in claim 17, wherein the composition or the object is paper, fabric, building materials, packaging materials, coating and paint compositions, disinfectants, detergents, household products, cosmetics or suncreams.

19. A method of inhibiting bacterial RNA polymerase and/or undecaprenyl pyrophosphate synthase, said method comprising contacting a cell with an effective amount of a compound as claimed in claim 1 or a pharmaceutically acceptable salt thereof.

20. A method of synthesizing a compound of the Formula I according to claim 1, wherein Y is a $C_1$ to $C_{10}$ alkyl, which comprises reacting a compound of Formula II with an amine of $R_4R_5NH$,

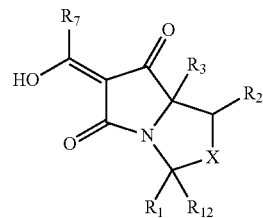

Formula II wherein:
- X is O, S or $SO_2$,
- Y is OH or $C_1$ to $C_{10}$ alkyl,
- $R_1$ and $R_2$ are each independently selected from H and $C_1$ to $C_6$ alkyl,
- $R_3$ is selected from a functional group selected from H, $C_1$ to $C_6$ alkyl, and a carbonyl-containing group,
- $R_{12}$ is H, alkenyl, aryl, trihaloalkyl, and $C_1$ to $C_6$ alkyl,
- $R_7$ is a group of the formula $L_1$-$L_2$-$R_6$ or $L_2$-$L_1$-$R_6$,
- where $L_1$ is a linker of the formula $—[CR_8R_9]_n—$, where n is an integer of from 0 to 12, and $R_8$ and $R_9$ are each independently selected from H or $C_1$ to $C_2$ alkyl, and
- where $L_2$ is absent or a linker that is selected from O, S, SO, $SO_2$, N(R'), C(O), C(O)O, OC(O), $[O(CR'_2)_r]_s$, $[(CR'_2)_rO]_s$ CH(OR'), C(O)N(R'), N(R')C(O), N(R')C(O)N(R'), $SO_2$N(R') or N(R')$SO_2$ where R' and R" are each independently selected from hydrogen and a $C_1$ to $C_2$ alkyl, and where r is 1 or 2 and s is 1 to 4, and
- where $R_6$ is selected from $OR^{13}$, heterocyclic and $C_1$ to $C_{25}$ hydrocarbyl group, wherein $R^{13}$ is a $C_1$ to $C_6$ alkyl, and said heterocyclic and hydrocarbyl group is optionally substituted with at least one functional group selected from alkenyl, alkyl, aryl, halo, trihaloalkyl, alcohol, keto, $S(O)R^{13}$, sulfonyl, thio-alcohol, ester, thioester, ether, thioether, amide, thioamide, urea, thiourea, =O, =S, amine and heterocyclic group.

21. A method of synthesizing a compound of the Formula Ia according to claim 2, which comprises
  a) reacting a compound of the formula III below

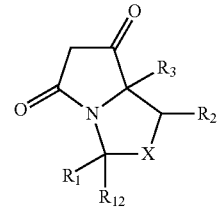

Formula III with a compound of the formula $R_5NCO$, or
  b) reacting a compound of the formula IV below

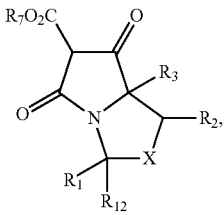

Formula IV with an amine of the formula $R_4R_5NH$, where $R_4$ is H.

22. The method as claimed in claim 21, wherein the compound of Formula IV is formed by acylating a compound of Formula III.

* * * * *